United States Patent
Gundlach et al.

(10) Patent No.: US 12,085,533 B2
(45) Date of Patent: Sep. 10, 2024

(54) NANOPORE-BASED ANALYSIS OF PROTEIN CHARACTERISTICS

(71) Applicant: University of Washington, Seattle, WA (US)

(72) Inventors: Jens H. Gundlach, Seattle, WA (US); Ian Michael Derrington, Seattle, WA (US); Andrew Laszlo, Seattle, WA (US); Jonathan Craig, Seattle, WA (US); Henry Brinkerhoff, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 18/475,534

(22) Filed: Sep. 27, 2023

(65) Prior Publication Data

US 2024/0085372 A1    Mar. 14, 2024

Related U.S. Application Data

(63) Continuation of application No. 17/202,118, filed on Mar. 15, 2021, now Pat. No. 11,808,734, which is a
(Continued)

(51) Int. Cl.
G01N 27/447    (2006.01)
G01N 33/487    (2006.01)
G01N 33/68     (2006.01)

(52) U.S. Cl.
CPC . *G01N 27/44743* (2013.01); *G01N 27/44791* (2013.01); *G01N 33/48721* (2013.01); *G01N 33/6818* (2013.01)

(58) Field of Classification Search
None
See application file for complete search history.

(56) References Cited

U.S. PATENT DOCUMENTS

| 7,189,503 B2 | 3/2007 | Akeson |
| 7,258,838 B2 | 8/2007 | Li et al. |

(Continued)

FOREIGN PATENT DOCUMENTS

| CN | 102834527 A | 12/2012 |
| CN | 103370617 A | 10/2013 |

(Continued)

OTHER PUBLICATIONS

Murphy, P.J., et al., "Single-Molecule Analysis of Combinatorial Epigenomic States in Normal and Tumor Cells," Proceedings of the National Academy of Sciences of the USA (PNAS) 110(19):7772-7777, May 2013.

(Continued)

*Primary Examiner* — Eli S Mekhlin
(74) *Attorney, Agent, or Firm* — Christensen O'Connor Johnson Kindness PLLC

(57) ABSTRACT

Methods for nanopore-based protein analysis are provided. The methods address the characterization of a target protein analyte, which has a dimension greater than an internal diameter of the nanopore tunnel, and which is also physically associated with a polymer. The methods further comprise applying an electrical potential to the nanopore system to cause the polymer to interact with the nanopore tunnel. The ion current through the nanopore is measured to provide a current pattern reflective of the structure of the portion of the polymer interacting with the nanopore tunnel. This is used as a metric for characterizing the associated protein that does not pass through the nanopore.

20 Claims, 7 Drawing Sheets

Specification includes a Sequence Listing.

Related U.S. Application Data continuation of application No. 16/517,996, filed on Jul. 22, 2019, now Pat. No. 10,948,454, which is a continuation of application No. 15/120,286, filed as application No. PCT/US2014/067732 on Nov. 26, 2014, now Pat. No. 10,359,395.

(60) Provisional application No. 61/941,919, filed on Feb. 19, 2014.

(56) References Cited

U.S. PATENT DOCUMENTS

| | | | |
|---|---|---|---|
| 7,504,058 | B1 | 3/2009 | Batten et al. |
| 7,846,738 | B2 | 12/2010 | Golovchenko |
| 8,273,532 | B2 | 9/2012 | Gershow |
| 8,324,914 | B2 | 12/2012 | Chen |
| 8,500,982 | B2 | 8/2013 | Akeson |
| 9,017,937 | B1 | 4/2015 | Turner et al. |
| 10,359,395 | B2 | 7/2019 | Gundlach et al. |
| 10,948,454 | B2 | 3/2021 | Gundlach et al. |
| 2004/0214177 | A1 | 10/2004 | Bension |
| 2012/0022792 | A1 | 1/2012 | Zysler et al. |
| 2012/0055792 | A1 | 3/2012 | Gundlach et al. |
| 2012/0094278 | A1 | 4/2012 | Akeson et al. |
| 2013/0071837 | A1 | 3/2013 | Winters-Hilt |
| 2013/0146456 | A1 | 6/2013 | Gundlach et al. |
| 2013/0146457 | A1 | 6/2013 | Gundlach et al. |
| 2013/0256139 | A1 | 10/2013 | Peng |
| 2014/0051068 | A1 | 2/2014 | Cherf et al. |

FOREIGN PATENT DOCUMENTS

| | | |
|---|---|---|
| CN | 103509852 A | 1/2014 |
| EP | 2 673 638 B1 | 10/2019 |
| EP | 3 074 534 B1 | 11/2019 |
| WO | 00/39333 A1 | 7/2000 |
| WO | 2006/092582 A1 | 9/2006 |
| WO | 2008/124107 A1 | 10/2008 |
| WO | 2009/035647 A1 | 3/2009 |
| WO | 2010/086603 A1 | 8/2010 |
| WO | 2011/046706 A1 | 4/2011 |
| WO | 2011/106456 A2 | 9/2011 |
| WO | 2011/106459 A2 | 9/2011 |
| WO | 2012/033524 A2 | 3/2012 |
| WO | 2013/014451 A1 | 1/2013 |
| WO | 2013/057495 A2 | 4/2013 |
| WO | 2013/083983 A1 | 6/2013 |
| WO | 2013/098562 A2 | 7/2013 |
| WO | 2013/153359 A1 | 10/2013 |
| WO | 2013/159042 A1 | 10/2013 |
| WO | 2014/013260 A1 | 1/2014 |
| WO | 2015/031909 A1 | 3/2015 |
| WO | 2015/051378 A1 | 4/2015 |

OTHER PUBLICATIONS

Nabel, C.S., et al., "The Curious Chemical Biology of Cytosine: Deamination, Methylation, and Oxidation as Modulators of Genomic Potential," ACS Chemical Biology 7(1):20-30, Jan. 2012.
Niederweis, M., et al., "Cloning of the MspA Gene Encoding a Porin From *Mycobacterium smegmatis*," Molecular Microbiology 33(5):933-945, Sep. 1999.
Olasagasti, F., et al., "Replication of Individual DNA Molecules Under Electronic Control Using a Protein Nanopore," Nature Nanotechnology 5(11):798-806, Nov. 2010.
Osaki, T., et al., "Multichannel Simultaneous Measurements of Single-Molecule Translocation in α-Hemolysin Nanopore Array," Analytical Chemistry 81(24):9866-9870, Dec. 2009.
Pastor, W.A., et al., "Genome-Wide Mapping of 5-Hydroxymethylcytosine in Embryonic Stem Cells," Nature 473(7347):394-397, May 2011.

Purnell, R.F., and J.J. Schmidt, "Discrimination of Single Base Substitutions in a DNA Strand Immobilized in a Biological Nanopore," ACS Nano 3(9):2533-2538, Sep. 2009.
Purnell, R.F., et al., "Nucleotide Identification and Orientation Discrimination of DNA Homopolymers Immobilized in a Protein Nanopore," Nano Letters 8(9):3029-3034, Aug. 2008.
Razin, A., and R. Shemer, "DNA Methylation in Early Development," Human Molecular Genetics 4:1751-1755, 1995.
Robertson, K.D., "DNA Methylation and Human Disease," Nature Reviews Genetics 6(8):597-610, Aug. 2005.
Salas, M., et al., "The Bacteriophage phi29 DNA Polymerase," IUBMB Life 60(1):82-85, Jan. 2008.
Sauer-Budge, A.F., et al., "Unzipping Kinetics of Double-Stranded DNA in a Nanopore," Physical Review Letters 90(23):238101, Jun. 2003.
Schibel, A.E., et al., "Nanopore Detection of 8-oxo-7,8-dihydro-2'-deoxyguanosine in Immobilized Single-Stranded DNA via Adduct Formation to the DNA Damage Site," Journal of the American Chemical Society 132(51):17992-17995, Dec. 2010.
Shendure, J.A., et al., "Overview of DNA Sequencing Strategies," in F.M. Ausubel et al. (eds.), "Current Protocols in Molecular Biology," Wiley InterScience, New York, Chap. 7, Unit 7.1, Jan. 2008, 11 pages.
Shendure, J., and H. Ji, "Next-Generation DNA Sequencing," Nature Biotechnology 26(10):1135-1145, Oct. 2008.
Shim, J., et al., "Detection and Quantification of Methylation in DNA Using Solid-State Nanopores," Scientific Reports 3:1389, 2013.
Silva, S.J., et al., "Mosaic Methylation in Clonal Tissue," Developmental Biology 156(2):391-398, Apr. 1993.
Skinner, M.K., et al., "Epigenetic Transgenerational Actions of Environmental Factors in Disease Etiology," Trends in Endocrinology and Metabolism 21(4):214-222, Apr. 2010.
Soni, G.V., and A. Meller, "Progress Toward Ultrafast DNA Sequencing Using Solid-State Nanopores," Clinical Chemistry 53(11):1996-2001, Nov. 2007.
Stoddart, D., et al., "Single-Nucleotide Discrimination in Immobilized DNA Oligonucleotides With a Biological Nanopore," Proceedings of the National Academy of Sciences of the USA (PNAS) 106(19):7702-7707, May 2009.
Tahiliani, M., et al., "Conversion of 5-Methylcytosine to 5-Hydroxymethylcytosine in Mammalian DNA by MLL Partner TET1," Science 324(5929):930-935, May 2009.
Thomson, J.P., et al., "Dynamic Changes in 5-Hydroxymethylation Signatures Underpin Early and Late Events in Drug Exposed Liver," Nucleic Acids Research 41(11):5639-5654, Jun. 2013.
van den Hout, M., et al., "Controlling Nanopore Size, Shape and Stability," Nanotechnology 21(11):115304, Mar. 2010.
Vercoutere, W., et al., "Rapid Discrimination Among Individual DNA Hairpin Molecules at Single-Nucleotide Resolution Using an Ion Channel," Nature Biotechnology 19(3):248-252, Mar. 2001.
Wallace, E.V., et al., "Identification of Epigenetic DNA Modifications With a Protein Nanopore," Chemical Communications 46(43):8195-8197, Nov. 2010.
Wanunu, M., "Nanopores: A Journey Towards DNA Sequencing," Physics of Life Reviews 9(2):125-158, Jun. 2012.
Wanunu, M., et al., "Discrimination of Methylcytosine From Hydroxymethylcytosine in DNA Molecules," Journal of the American Chemical Society 133(3):486-492, Jan. 2011.
Wilson, N.A., et al., "Electronic Control of DNA Polymerase Binding and Unbinding to Single DNA Molecules," ACS Nano 3(4):995-1003, Apr. 2009.
Yu, M., et al., "Base-Resolution Analysis of 5-Hydroxymethylcytosine in the Mammalian Genome," Cell 149(6):1368-1380, Jun. 2012.
First Written Opinion completed Jun. 6, 2017, issued in in Singapore Application No. 11201607796T, filed Nov. 26, 2014, 8 pages.
Communication mailed Jul. 6, 2022, issued in EP Application No. 14883310.6, filed Nov. 26, 2014, 8 pages.
Arnaut, V., et al., "Nanopore Force Spectroscopy of Aptamer-Ligand Complexes," Biophysical Journal 105(5):1199-1207, Sep. 2013.

(56) References Cited

OTHER PUBLICATIONS

Bosco, A., et al., "Elastic Properties and Secondary Structure Formation of Single-Stranded DNA at Monovalent and Divalent Salt Conditions," Nucleic Acids Research 42(3):2064-2074, Feb. 2014.
Branton, D., et al., "The Potential and Challenges of Nanopore Sequencing," Nature Biotechnology 26(10):1146-1153, Oct. 2008.
Butler, T.Z., et al., "Single-Molecule DNA Detection With an Engineered MspA Protein Nanopore," Proceedings of the National Academy of Sciences USA (PNAS) 105(52):20647-20652, Dec. 2008.
Cheng, W., et al., "NS3 Helicase Actively Separates RNA Strands and Senses Sequence Barriers Ahead of the Opening Fork," Proceedings of the National Academy of Sciences USA (PNAS) 104(35):13954-13959, Aug. 2007.
Cressiot, B., et al., "Protein Transport Through a Narrow Solid-State Nanopore at High Voltage: Experiments and Theory," ACS Nano 6(7):6236-6243, Jul. 2012.
Derrington, I.M., et al., "Nanopore DNA Sequencing With MspA," Proceedings of the National Academy of Sciences USA (PNAS) 107(37):16060-16065, Sep. 2010.
Dessinges, M.-N., et al., "Single-Molecule Assay Reveals Strand Switching and Enhanced Processivity of UvrD," Proceedings of the National Academy of Sciences USA (PNAS) 101(17):6439-6444, Apr. 2004.
Evans, D.A., et al., "The Asymmetric Synthesis of α-Amino Acids. Electrophilic Azidation of Chiral Imide Enolates, a Practical Approach to the Synthesis of (R)- and (S)-α-Azido Carboxylic Acids," Journal of the American Chemical Society 112(10):4011-4030, May 1990.
Johnson, D.S., et al., "Single-Molecule Studies Reveal Dynamics of DNA Unwinding by the Ring-Shaped T7 Helicase," Cell 129(7):1299-1309, Jun. 2007.
Laszlo, A.H., et al., "Decoding Long Nanopore Sequencing Reads of Natural DNA," Nature Biotechnology 32(8):829-833, Aug. 2014.
Laszlo, A.H., et al., "Detection and Mapping of 5-Methylcytosine and 5-Hydroxymethylcytosine With Nanopore MspA," Proceedings of the National Academy of Sciences USA (PNAS) 110(47):18904-18909, Nov. 2013.
Lionnet, T., et al., "Real-Time Observation of Bacteriophage T4 gp41 Helicase Reveals an Unwinding Mechanism," Proceedings of the National Academy of Sciences USA (PNAS) 104(50):19790-19795, Dec. 2007.
Manrao, E.A., et al., "Nucleotide Discrimination With DNA Immobilized in the MspA Nanopore," PLoS ONE 6(10):e25723, Oct. 2011, 7 pages.
Manrao, E.A., et al., "Reading DNA at Single-Nucleotide Resolution With a Mutant MspA Nanopore and phi29 DNA Polymerase," Nature Biotechnology 30(4):349-354, Apr. 2012.
Marsden, S., et al., "Unwinding Single RNA Molecules Using Helicases Involved in Eukaryotic Translation Initiation," Journal of Molecular Biology 361(2):327-335, Aug. 2006.
Myong, S., et al., "Spring-Loaded Mechanism of DNA Unwinding by Hepatitis C Virus NS3 Helicase," Science 317(5837):513-516, Jul. 2007.
Perkins, T.T., et al., "Forward and Reverse Motion of Single RecBCD Molecules on DNA," Biophysical Journal 86(3):1640-1648, Mar. 2004.
Pu, Y., et al., "Synthesis and Acylation of Salts of L-Threonine β-Lactone: A Route to β-Lactone Antibiotics," Journal of Organic Chemistry 56(3):1280-1283, Feb. 1991.
Rotem, D., et al., "Protein Detection by Nanopores Equipped With Aptamers," Journal of the American Chemical Society 134(5):2781-2787, Feb. 2012.
Smith, S.B., et al., "Overstretching B-DNA: The Elastic Response of Individual Double-Stranded and Single-Stranded DNA Molecules," Science 271(5250):795-799, Feb. 1996.
Sun, B., et al., "Impediment of E. coli UvrD by DNA-Destabilizing Force Reveals a Strained-Inchworm Mechanism of DNA Unwinding," EMBO Journal 27(24):3279-3287, Dec. 2008.

Theissen, B., et al., "Cooperative Binding of ATP and RNA Induces a Closed Conformation in a DEAD Box RNA Helicase," Proceedings of the National Academy of Sciences USA (PNAS) 105(2):548-553, Jan. 2008.
Williams, G.T., et al., "E1a Transactivation of the Human HSP70 Promoter is Mediated Through the Basal Transcriptional Complex," Molecular and Cellular Biology 9(6):2574-2587, Jun. 1989.
Williams, R.M., and M.-N. IM, "Asymmetric Synthesis of Monosubstituted and α,α-Disubstituted α-Amino Acids via Diastereoselective Glycine Enolate Alkylations," Journal of the American Chemical Society 113(24):9276-9286, Nov. 1991.
Winters-Hilt, S., "Nanopore Detector Based Analysis of Single Molecule Conformational Kinetics and Binding Interactions," BMC Bioinformatics 7(Suppl 2):S21, Sep. 2006, 27 pages.
Yodh, J.G., et al., "Insight Into Helicase Mechanism and Function Revealed Through Single-Molecule Approaches," Quarterly Reviews of Biophysics 43(2):185-217, May 2010.
Zhang, X., et al., "Single Molecule Analysis of Light-Regulated RNA:Spiropyran Interactions," Chemical Science 5(7):2642-2646, Jul. 2014.
Fologea, D., et al., "Electrical Characterization of Protein Molecules by a Solid-State Nanopore," Applied Physics Letters 91(5):053901-1-053901-3, Jul. 2007.
Kuwada, N.J., et al., "A Master Equation Approach to Modeling an Artificial Protein Motor," Chemical Physics 91(2-3):1-3, Oct. 2010.
Written Opinion and International Search Report mailed Mar. 10, 2015, issued in corresponding International Application No. PCT/US2014/067732, filed Nov. 26, 2014, 11 pages.
International Preliminary Examination Report mailed Sep. 1, 2016, issued in corresponding International Application No. PCT/US2014/067732, filed Nov. 26, 2014, 11 pages.
Geng, J., et al., "Channel Size Conversion of Phi29 DNA-Packaging Nanomotor for Discrimination of Single- and Double-Stranded Nucleic Acids," ACS NANO 7(4):3315-3323, Mar. 15, 2013 [online].
Supplementary European Search Report mailed Aug. 3, 2017, issued in European Patent Application No. 14883310.6, filed Nov. 26, 2014, 6 pages.
Chinese Office Action mailed May 3, 2018, issued in corresponding Chinese Application No. 201480077395.3, filed Nov. 26, 2014, 20 pages.
Akeson, M., et al., "Microsecond Time-Scale Discrimination Among Polycytidylic Acid, Polyadenylic Acid, and Polyuridylic Acid as Homopolymers or as Segments Within Single RNA Molecules," Biophysical Journal 77(6):3227-3233, Dec. 1999.
Amundadottir, L.T., et al., "A Common Variant Associated With Prostate Cancer in European and African Populations," Nature Genetics 38(6):652-658, Jun. 2006.
Aran, D., et al., "DNA Methylation of Distal Regulatory Sites Characterizes Dysregulation of Cancer Genes," Genome Biology 14(3):R21, Mar. 2013.
Ashkenasy, N., et al., "Recognizing a Single Base in an Individual DNA Strand: A Step Toward DNA Sequencing in Nanopores," Angewandte Chemie International Edition 44(9):1401-1404, Feb. 2005.
Benner, S., et al., "Sequence-Specific Detection of Individual DNA Polymerase Complexes in Real Time Using a Nanopore," Nature Nanotechnology 2(11):718-724, Nov. 2007.
Bentley, D.R., "Whole-Genome Re-Sequencing," Current Opinion in Genetics & Development 16(6):545-552, Dec. 2006.
Bird, A., "Perceptions of EpiGenetics" Nature 447(7143):396-398, May 2007.
Blanco, L., and M. Salas, "Relating Structure to Function in phi29 DNA Polymerase," Journal of Biological Chemistry 271(15):8509-8512, Apr. 1996.
Blanco, L., et al., "Highly Efficient DNA Synthesis by Phage phi29 DNA Polymerase," Journal of Biological Chemistry 264(15):8935-8940, May 1989.
Booth, M.J., et al., "Quantitative Sequencing of 5-Methylcytosine and 5-Hydroxymethylcytosine at Single-Base Resolution," Science 336(6083):934-937, May 2012.
Cherf, G.M., et al., "Automated Forward and Reverse Ratcheting of DNA in a Nanopore at Five Angstrom Precision," Nature Biotechnology 30(4):344-348, Feb. 2012.

(56) References Cited

OTHER PUBLICATIONS

Churbanov, A., et al., "Duration Learning for Analysis of Nanopore Ionic Current Blockades," BMC Bioinformatics 8(Suppl 7):S14, Nov. 2007.
Clark, T.A., et al., "Enhanced 5-Methylcytosine Detection in Single-Molecule, Real-Time Sequencing via Tet1 Oxidation," BMC Biology 11:4, Jan. 2013.
Cockroft, S.L., et al., "A Single-Molecule Nanopore Device Detects DNA Polymerase Activity With Single-Nucleotide Resolution," Journal of the American Chemical Society 130(3):818-820, Jan. 2008.
Cokus, S.J., et al., "Shotgun Bisulphite Sequencing of the *Arabidopsis* Genome Reveals DNA Methylation Patterning," Nature 452(7184):215-219, Mar. 2008.
Das, P.M., and R. Singal, "DNA Methylation and Cancer," Journal of Clinical Oncology 22(22):4632-4642, Nov. 2004.
Drmanac, R., et al., "Human Genome Sequencing Using Unchained Base Reads on Self-Assembling DNA Nanoarrays," Science 327(5961):78-81, Nov. 2009.
Easton, D.F., et al., "Genome-Wide Association Study Identifies Novel Breast Cancer Susceptibility loci," Nature 447(7148):1087-1093, Jun. 2007.
Eid, J., et al., "Real-Time DNA Sequencing From Single Polymerase Molecules," Science 323(5910):133-138, Jan. 2009.
Faller, M., et al., "The Structure of a Mycobacterial Outer-Membrane Channel," Science 303(5661):1189-1192, Feb. 2004.
Flusberg, B.A., et al., "Direct Detection of DNA Methylation During Single-Molecule, Real-Time Sequencing," Nature Methods 7(6):461-465, Jun. 2010.
Freedman, M.L., et al., "Admixture Mapping Identifies 8q24 as a Prostate Cancer Risk locus in African-American Men," Proceedings of the National Academy of Sciences USA (PNAS) 103(38):14068-14073, Sep. 2006.
Fuller, C.W., et al., "The Challenges of Sequencing by Synthesis," Nature Biotechnology 27(11):1013-1023, Nov. 2009.
Gal-Yam, E.N., et al., "Cancer Epigenetics: Modifications, Screening, and Therapy," Annual Review of Medicine 59:267-280, Feb. 2008.
Goldstein, D.B., "Common Genetic Variation and Human Traits," New England Journal of Medicine 360(17):1696-1698, Apr. 2009.
Gyarfas, B., et al., "Mapping the Position of DNA Polymerase-Bound DNA Templates in a Nanopore at 5 Å Resolution," ACS Nano 3(6):1457-1466, Jun. 2009.
Heyn, H.E., and M. Esteller, "DNA Methylation Profiling in the Clinic: Applications and Challenges," Nature Reviews Genetics 13(10):679-692, Oct. 2012.
Hirschhorn, J.N., "Genomewide Association Studies—Illuminating Biologic Pathways," New England Journal of Medicine 360(17):1699-1701, Apr. 2009.
Hurt, N., et al., "Specific Nucleotide Binding and Rebinding to Individual DNA Polymerase Complexes Captured on a Nanopore," Journal of the American Chemical Society 131(10):3772-3778, Mar. 2009.
Ibarra, B., et al., "Proofreading Dynamics of a Processive DNA Polymerase," EMBO Journal 28(18):2794-2802, Sep. 2009.
Iqbal, K., et al., "Reprogramming of the Paternal Genome Upon Fertilization Involves Genome-Wide Oxidation of 5-Methylcytosine," Proceedings of the National Academy of Sciences USA (PNAS) 108(9):3642-3647, Mar. 2011.
Irizarry, R.A., et al., "Comprehensive High-Throughput Arrays for Relative Methylation (CHARM)," Genome Research 18(5):780-790, May 2008.
Ito, S., et al., "Tet Proteins Can Convert 5-Methylcytosine to 5-Formylcytosine and 5-Carboxylcytosine," Science 333(6047):1300-1303, Sep. 2011.
Jin, S.G., et al., "Examination of the Specificity of DNA Methylation Profiling Techniques Towards 5-Methylcytosine and 5-Hydroxymethylcytosine," Nucleic Acids Research 38(11):e125, Jun. 2010.
Kahvejian, A., et al., "What Would You Do if You Could Sequence Everything?" Nature Biotechnology 26(10):1125-1133, Oct. 2008.
Kasianowicz, J.J., et al., "Characterization of Individual Polynucleotide Molecules Using a Membrane Channel," Proceedings of the National Academy of Sciences of the USA (PNAS) 93(24):13770-13773, Nov. 1996.
Khulan, B., et al., "Comparative Isoschizomer Profiling of Cytosine Methylation: The HELP Assay," Genome Research, 16(8):1046-1055, Aug. 2006.
Kim, Y.R., et al., "Detecting Translocation of Individual Single Stranded DNA Homopolymers Through a Fabricated Nanopore Chip," Frontiers in Bioscience 12:2978-2983, May 2007.
Kriaucionis, S., and N. Heintz, "The Nuclear DNA Base 5-Hydroxymethylcytosine is Present in Purkinje Neurons and the Brain," Science 324(5929):929-930, May 2009.
Laird, P.W., "Principles and Challenges of Genome-Wide DNA Methylation Analysis," Nature Reviews: Genetics 11(3):191-203, Mar. 2010.
Lee, J.W., and A. Meller, "Rapid DNA Sequencing by Direct Nanoscale Reading of Nucleotide Bases on Individual DNA Chains: New High Throughput Technologies for DNA Sequencing and Genomics," in K. Mitchelson (ed.), "Perspectives in Bioanalysis," vol. 2, Chap. 8, Elsevier, Oxford, pp. 245-264, 2007.
Li, J., et al., "DNA Molecules and Configurations in a Solid-State Nanopore Microscope," Nature Materials 2(9):611-615, Sep. 2003.
Lieberman, K.R., et al., "Processive Replication of Single DNA Molecules in a Nanopore Catalyzed by phi29 DNA Polymerase," Journal of the American Chemical Society 132(50):17961-17972, Dec. 2010.
Lluch-Senar, M., et al., "Comprehensive Methylome Characterization of *Mycoplasma genitalium* and *Mycoplasma pneumoniae* at Single-Base Resolution," PLoS Genetics 9(1):e1003191, Jan. 2013.
Marx, V., "Epigenetics: Reading the Second Genomic Code," Nature 491(7422):143-147, Nov. 2012.
McNally, B., et al., "Optical Recognition of Converted DNA Nucleotides for Single-Molecule DNA Sequencing Using Nanopore Arrays," Nano Letters 10(6):2237-2244, Jun. 2010.
Mellén, M., et al., "MeCP2 Binds to 5hmC Enriched Within Active Genes and Accessible Chromatin in the Nervous System," Cell 151(7):1417-1430, Dec. 2012.
Meller, A., et al., "Rapid Nanopore Discrimination Between Single Polynucleotide Molecules," Proceedings of the National Academy of Sciences of the USA (PNAS) 97(3):1079-1084, Feb. 2000.
Mitchell, N., and S. Howorka, "Chemical Tags Facilitate the Sensing of Individual DNA Strands With Nanopores," Angewandte Chemie International Edition 47(30):5565-5568, Jul. 2008.
Morris, J.R., et al., "The SUMO Modification Pathway is Involved in the BRCA1 Response to Genotoxic Stress," Nature 462(7275):886-890, Dec. 2009.

NANOPORE-BASED ANALYSIS OF PROTEIN CHARACTERISTICS

CROSS-REFERENCES TO RELATED APPLICATIONS

This application is a continuation of U.S. patent application Ser. No. 17/202,118, filed Mar. 15, 2021, which is a continuation of U.S. patent application Ser. No. 16/517,996, filed Jul. 22, 2019, which is a continuation of U.S. patent application Ser. No. 15/120,286, filed Aug. 19, 2016 (now U.S. patent Ser. No. 10/359,395), which is the national stage of International Application No. PCT/US2014/067732, filed Nov. 26, 2014, which claims the benefit of U.S. Provisional Patent Application No. 61/941,919, filed Feb. 19, 2014, each of which applications is incorporated herein by reference in its entirety.

STATEMENT OF GOVERNMENT LICENSE RIGHTS

This invention was made with Government support under R01HG005115 awarded by the National Human Genome Research Institute (NHGRI) of the National Institutes of Health. The Government has certain rights in the invention.

STATEMENT REGARDING SEQUENCE LISTING

The sequence listing associated with this application is provided in XML format in lieu of a paper copy and is hereby incorporated by reference into the specification. The name of the XML file containing the sequence listing is 3915-P808USCON3UW_Seq_List_20230821.xml. The XML file is 3,757 bytes; was created on Aug. 21, 2023; and is being submitted herewith via Patent Center with the filing of the specification.

BACKGROUND

The ability to provide a fine-scale characterization of protein conformation and movement can provide a wealth of information regarding the protein's function. Several techniques have been developed to provide a great advancement in resolution of such functional protein studies. Assays that incorporate Forster Resonance Energy Transfer (FRET) provide detectable signals when moieties attached to predetermined protein domains interact within a spatial range. However, FRET signals are generated in bulk assays that aggregate signals from a large number of individual interactions and, thus, are inherently limited in resolution. Other assays avoid the data scatter inherent to bulk assays by addressing the interactions of single-molecules. For example, commonly used tools to conduct measurements on motor enzymes include optical tweezers, magnetic tweezers, tethered particle assays. For example, optical tweezers employ a highly focused laser beam to hold (or repulse) an object, such as a bead. The bead can be attached to a polymer that functions as a tether. The polymer can then be manipulated by a target enzyme that interacts (i.e., applies force) to the polymer. These manipulations are detected by measuring the displacement of the bead (or other object) from the field applied by the laser. To date, optical tweezers can achieve a precision of ~0.3 nm spatial resolution at ~1 ms time scales without ensemble averaging. The limitation of this resolution is due, in part, to the long tether of the polymer required to avoid damaging the target protein by the applied laser.

The ability to observe the mechanistic functioning of complex bio-molecules directly, and not just via the input and output of bulk assays, can accelerate health care and address how biological systems really work. However, notwithstanding the advances of single-molecule techniques, a need remains for inexpensive and facile techniques that can address mechanistic movements and conformation states of proteins at improved spatial and temporal resolutions.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter. This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, this disclosure provides a method of characterizing a protein in a nanopore system. The nanopore system comprises a nanopore disposed in a membrane that separates a first conductive liquid medium from a second conductive liquid medium, wherein the nanopore comprises a tunnel that provides liquid communication between the first conductive liquid medium and the second conductive liquid medium, and wherein the protein is physically associated with a polymer in the first conductive liquid medium. The method comprises:

(a) applying an electrical potential between the first conductive liquid medium and the second conductive liquid medium to cause the polymer to interact with the nanopore tunnel, wherein at least one dimension of the protein exceeds a diameter of the nanopore tunnel;

(b) measuring an ion current through the nanopore during the interaction of the polymer with the nanopore tunnel to provide a current pattern;

(c) determining a position and/or movement of at least one polymer subunit in the nanopore tunnel from the current pattern; and (d) associating the position and/or movement of the at least one polymer subunit with a characteristic of the protein.

In one embodiment, the polymer is a nucleic acid, PNA, or a combination thereof. In one embodiment, the nucleic acid is DNA, RNA, or a combination thereof. In one embodiment, the nucleic acid comprises an abasic residue. In one embodiment, the nucleic acid is not a homopolymer.

In one embodiment, the protein is an enzyme. In one embodiment, the enzyme is a molecular motor. In one embodiment, the molecular motor is a translocase, a polymerase, a helicase, an exonuclease, a viral packaging motor, or a topoisomerase. In one embodiment, the enzyme is a Brownian motor, Brownian ratchet ribosome, myosin, or kinesin. In one embodiment, the protein is a mutant protein or fusion protein. In one embodiment, the protein comprises two or more domains capable of mutual interaction. In one embodiment, the protein is covalently coupled to the polymer.

In one embodiment, the position and/or movement of the at least one polymer subunit can be resolved to about 35 pm. In one embodiment, the position of the at least one polymer subunit is associated with a conformational state of the protein. In one embodiment, the movement of the at least one polymer subunit is associated with a length of a discrete translocation step of the polymer within the nanopore tunnel that is conferred by the molecular motor. In one embodiment, the movement of the at least one polymer subunit is associated with a temporal duration of a discrete translocation step of the polymer within the nanopore tunnel that is conferred by the molecular motor. The temporal duration can be resolved to about 800 ns. In one embodiment, the movement of the at least one polymer subunit is associated with an incidence rate of polymer translocation missteps committed by the molecular motor. In one embodiment, the characteristic of the enzyme is a presence or degree of modulation of enzyme activity conferred by a reaction condition or putative agonist, antagonist, or co-factor.

In one embodiment, the nanopore is a solid-state nanopore, a protein nanopore, a hybrid solid state-protein nanopore, a biologically adapted solid-state nanopore, or a DNA origami nanopore. In one embodiment, the protein nanopore is alpha-hemolysin, leukocidin, *Mycobacterium smegmatis* porin A (MspA), outer membrane porin F (OmpF), outer membrane porin G (OmpG), outer membrane phospholipase A, *Neisseria* autotransporter lipoprotein (NalP), WZA, *Nocardia farcinica* NfpA/NfpB cationic selective channel, lysenin or a homolog or variant thereof. In one embodiment, the protein nanopore sequence is modified to contain at least one amino acid substitution, deletion, or addition. In one embodiment, the at least one amino acid substitution, deletion, or addition results in a net charge change in the nanopore. In one embodiment, the protein nanopore has a constriction zone with a non-negative charge.

In one embodiment, the electrical potential applied is between 10 mV and 1 V or between −10 mV and −1 V.

In another aspect, the disclosure provides a method of characterizing a protein in a nanopore system. The comprises a nanopore disposed in a membrane that separates a first conductive liquid medium from a second conductive liquid medium, wherein the nanopore comprises a tunnel that provides liquid communication between the first conductive liquid medium and the second conductive liquid medium, and wherein the protein is physically associated with a polymer in the first conductive liquid medium. The method comprises:

(a) applying an electrical potential between the first conductive liquid medium and the second conductive liquid medium to cause the polymer to interact with the nanopore tunnel, wherein at least one dimension of the protein exceeds a diameter of the nanopore tunnel;

(b) measuring an ion current through the nanopore during the interaction of the polymer with the nanopore tunnel to provide a first current pattern;

(c) comparing the first current pattern to a reference current pattern;

(d) determining a change in position and/or movement of at least one polymer subunit in the nanopore tunnel from the position and/or movement of at least one polymer subunit in the nanopore tunnel determined from the reference current pattern; and (e) associating the change in position and/or movement of the at least one polymer subunit in the nanopore tunnel with a characteristic of the enzyme.

In one embodiment, the nanopore system comprises a difference from the nanopore system used to generate the reference current pattern. In one embodiment, the difference is the presence or absence of a putative protein agonist, antagonist, or co-factor in the first conductive medium. In one embodiment, the difference is a difference concentration of a putative protein agonist, antagonist, or co-factor in the first conductive medium. In one embodiment, the characteristic is a presence or degree of modulation of protein activity or conformation conferred by the putative agonist, antagonist, or co-factor. In one embodiment, the difference is at least one amino acid difference in the amino acid sequence of the protein compared to the amino acid protein sequence in the nanopore system used to generate the reference current pattern. In one embodiment, the characteristic is a presence or degree of modulation of protein activity or conformation conferred by the amino acid difference in the amino acid sequence. In one embodiment, the method further comprises generating a reference current pattern.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A graphically illustrates the current levels (solid black lines) corresponding to the shown DNA sequence sequence (set forth as SEQ ID NO:1), which provide a distance measure (in nt). A spline profile (curved line) is used to demonstrate distances in between levels. The standard deviation of the current levels yield the precision to which distances can be measured. X in the indicated sequence represents an abasic residue. FIG. 2B is a cartoon illustration of DNA moving within the constriction of MspA by a distance 6.

FIG. 2C graphically illustrates current levels corresponding to the shown DNA sequence (set forth as SEQ ID NO:2) observed from the nanopore system at 180 mV (circles), and at 140 mV (triangles). FIG. 2D graphically illustrates current values for 180 mV (circles) and a spline fit to those levels (dotted curve). Triangles present the levels taken at 140 mV, as illustrated in FIG. 2C, after a multiplicative scale and additive offset. For the scaled 140 mV levels, the horizontal position is displaced by 0.3 nt to put the levels in-line with the spline profile for the current levels observed at 180 mV. This indicates the applied voltage shifts the DNA within MspA by 0.3 nt. FIG. 2E illustrates the corresponding observed time-ordered mean ion current levels derived from the original current pattern where the DNA was moved by phi29 DNAP. The levels correspond to the DNA sequence (set forth as SEQ ID NO:3) and hence, the physical displacement of the DNA sequence relative to MspA. A dashed line overlays current levels to indicate the current profile corresponding to the specific DNA sequence when moving continuously through the nanopore. FIG. 2F graphically illustrates the observed time-ordered mean ion current levels derived from the original current pattern where the same DNA (set forth as SEQ ID NO:3) was moved by hel308 TGA. When DNA motion is controlled by the translocase activity of hel308 TGA, a level profile directly comparable to that generated by DNA translocation controlled by phi29 DNAP is observed. However, the hel308 TGA current pattern shows twice as many levels for the same DNA sequence. This suggests that hel308 TGA moves DNA twice per nucleotide, relative to MspA.

FIG. 3A graphically illustrates a consensus current level pattern generated in a nanopore system for a DNA polymer associated with phi29 DNA polymerase.

FIG. 3B graphically illustrates a consensus current level pattern generated in the same nanopore system for the same DNA polymer as in FIG. 3A, but where the DNA is associated with the helicase hel308 TGA. Each one-nucleotide translation along the DNA is divided into two distinct steps, compared to FIG. 3A. All helicase data are taken at the experimental conditions of 22° C., 300 mM KCl, 5 mM $MgCl_2$ and 180 mV.

FIG. 3C graphically illustrates the half-life of current levels indicated in FIG. 3B. The level duration alternates between long and short durations. The duration of every other level is dependent on ATP concentration ("[ATP]"), as determined by using different concentrations of ATP: 10 μM ATP (dashed lines) and 1000 μM ATP (solid lines).

FIG. 3D graphically illustrates that the difference of the durations with high and with low [ATP] removes sequence dependence that also influences the step durations.

FIG. 3E graphically illustrates the average durations of levels versus $[ATP]^{-1}$ for ATP-independent steps (long dashed lines) and the ATP-dependent steps (short dashed lines). For the ATP-independent steps we measured an average rate of 4.5+/0.4 $s^{-1}$. For the ATP-dependent steps, we observed Michaelis Menton kinetics with a maximum velocity of 15.2+/−1.3/s and the Michaelis constant of 92.5+/−9.9 μmol.

FIG. 3F graphically illustrates that half-life of levels depend on the identity of the nucleotide that had passed through the constriction: A=alternating long-short dash, C=solid, G=light, short dash, T=heavy, long dash; the lower set of lines represent the ATP-dependent steps and upper set represent the ATP-independent steps with [ATP] at 500 μM. The peaks at 14, 17, and 18 indicate positions located within the enzyme where G, T, or C's, respectively, cause longer level durations.

FIG. 3G graphically illustrates the phase of steps relative to the phi29 DNAP. The ATP-independent steps are represented as solid bars and the ATP-dependent steps are represented in open bars. The average hel308 step length between ATP-independent and ATP-dependent steps is 0.53±0.04 nt. Average uncertainties are standard deviations of the mean. The ion current uncertainties for the levels means illustrated in FIG. 3A are, on average smaller, than the line width, <0.1 pA.

DETAILED DESCRIPTION

Figure 1A:
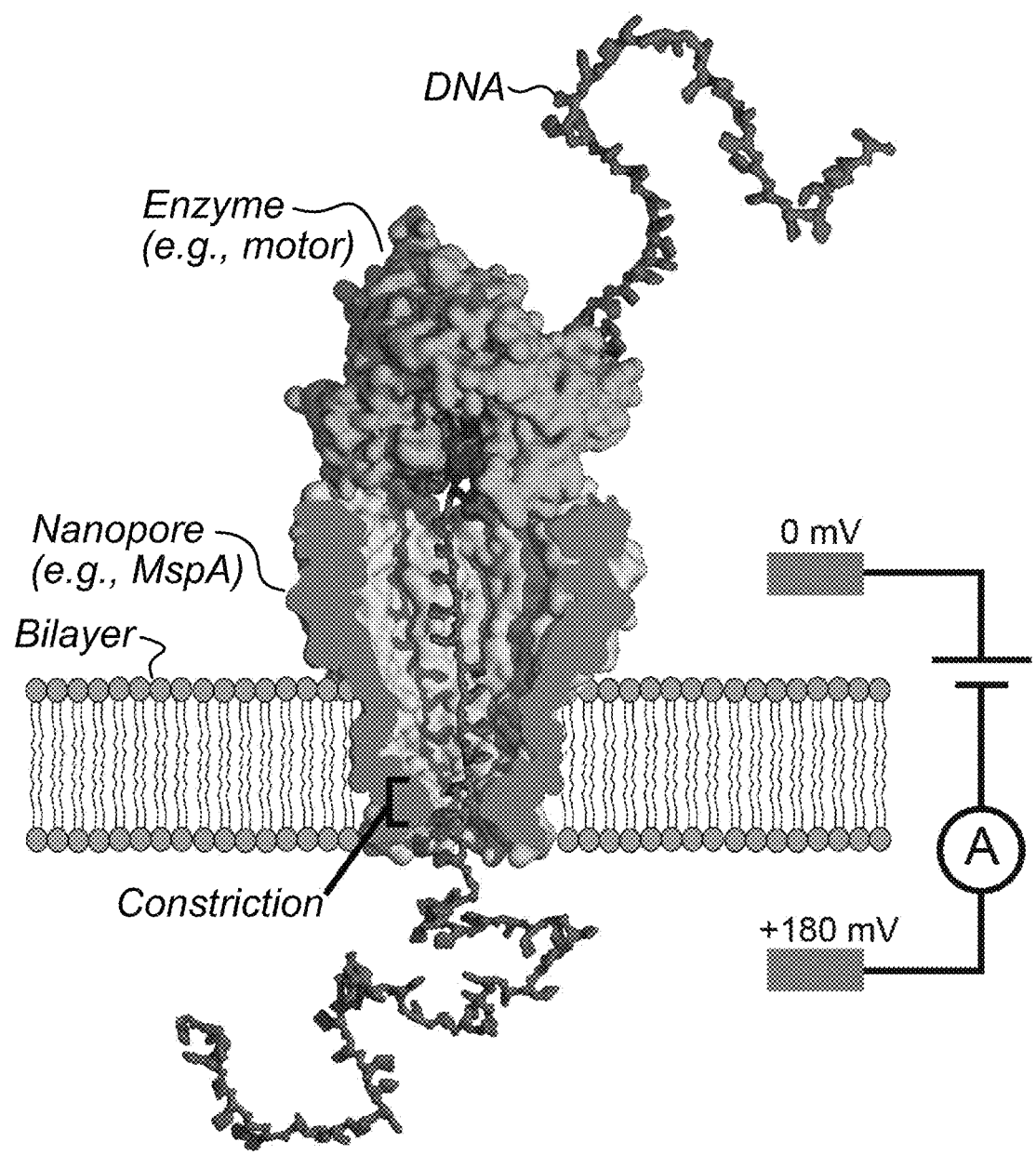
FIG. 1A is a cartoon illustration of an exemplary nanopore system useful in the practice of the present disclosure. Schematically, a single nanopore (e.g., MspA) is embedded in a phospholipid bilayer that separates two volumes of conductive liquid media, such as an electrolyte mixture. A voltage across the bilayer causes an ion current to flow through the interior of the nanopore. A protein, such as a molecular motor enzyme, is physically associated with a polymer (e.g., DNA) that is drawn to the interior of the nanopore. The single stranded end passes into and through the nanopore until the protein, which exceeds the largest diameter of the interior tunnel of the nanopore, comes to rest on the pore. The ion current in the nanopore tunnel is influenced by the nucleotide structures (thus identity) within the narrowest portion of the nanopore tunnel ("constriction").
Figure 1B:
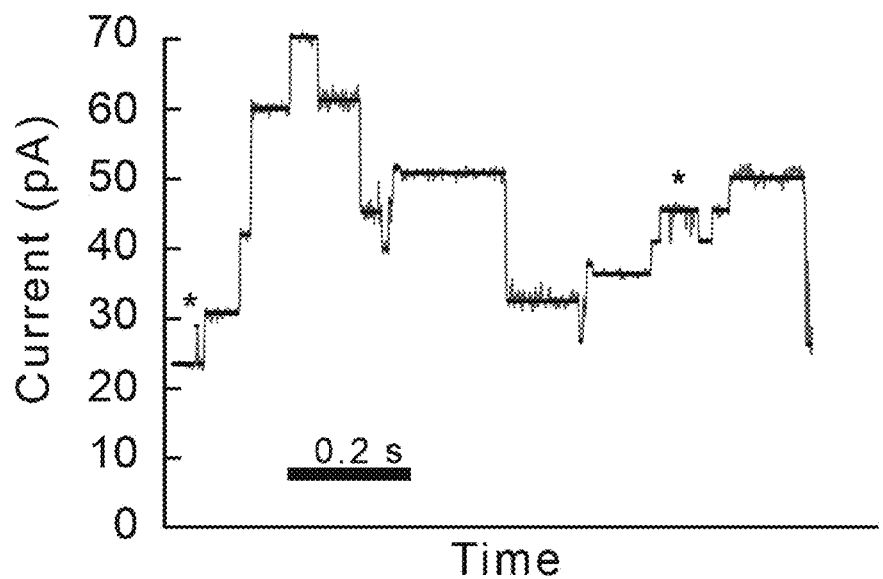
FIG. 1B is a graphical illustration of a representative current pattern produced by a nanopore system using an MspA nanopore and DNA associated with a phi29 DNA polymerase enzyme. The current pattern indicates that the DNA is moved through the nanopore by the phi29 DNA polymerase (DNAP) enzyme in discrete translocation steps. The observed current levels can be associated with DNA sequence. Occasional back-stepping activity of the phi29 DNAP causes repetitions of levels indicated by *.
Figure 1C:
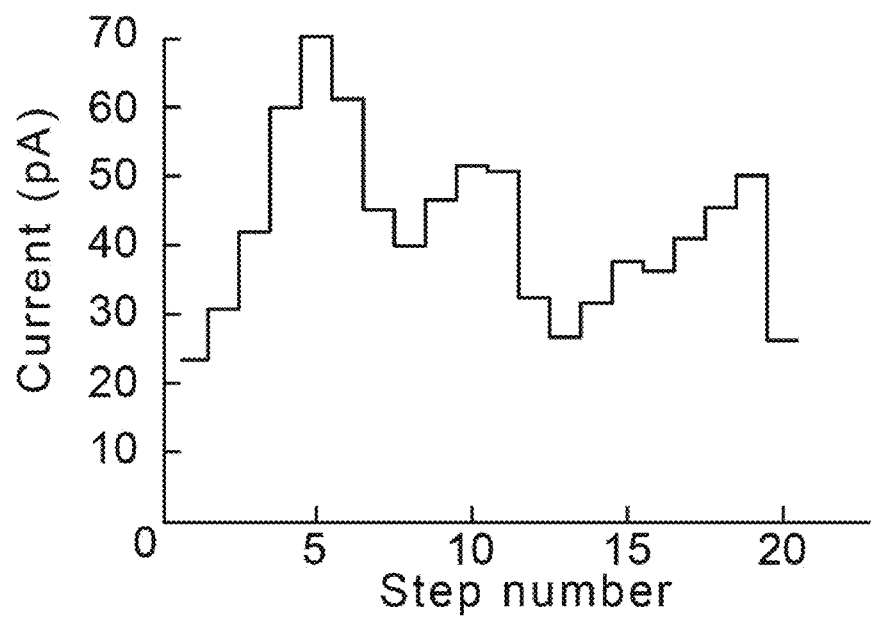
FIG. 1C is a graphical representation of the time-ordered mean ion current values derived from the original, stochastic level durations.

The present disclosure relates to the inventors' advancements to the analysis and characterization of target proteins using nanopore based systems.

Nanopore systems have been previously employed to characterize a variety of analytes, such as small molecules and polymers. These methods generally involve passing the target analyte through a nanoscopic opening while monitoring a detectable signal, such as an electrical signal. The signal is influenced by the physical properties of the target analyte as it passes through the nanopore and, thus, can be associated with a structural feature of the analyte, such as its identity. When addressing polymeric analytes, for example, single-stranded DNA ("ssDNA"), the discrete detectable signals can be influenced by the structure of each consecutive polymer subunit when the polymer passes linearly through the nanopore, thus providing information regarding the sequence of the polymer.

The present inventors have co-opted the above nanopore system approach to investigate larger analytes that are unable to pass through the nanopore opening, instead of small analytes that can enter the interior space of the nanopore. As described in more detail below, the inventors discovered that important features of larger protein analytes can be characterized using nanopore systems, notwithstanding the fact that they do not pass through the nanopore. Briefly stated, in this novel approach a polymer is associated with the target protein. As the polymer interacts with the interior of the nanopore tunnel, the associated protein is pulled toward the opening rim of the nanopore but cannot pass through due to its size. Using this information, the polymer can now be used as a measurement tool to ascertain a distance between the nanopore constriction zone and the target protein to a resolution as small as 30-40 picometers. Furthermore, the polymer-protein association need not be static, but can be dynamic. In this case, the polymer's movements through the nanopore can be monitored in real time with a resolution shorter than a millisecond, such as to about 700 microseconds or 800 microseconds. Accordingly, a wide variety of protein characteristics can be investigated at spatial and temporal resolutions heretofore unseen in existing technologies, such as with molecular tweezers and FRET analysis. As will be discussed, the nanopore system can be configured to address a wide variety of protein characteristics, such as the nature of folding and conformational changes, the structural and conformational effects of mutations in protein sequence, and the nature of molecular motor-polymer interactions. Moreover, these experimental configurations can be applied to broader investigations of potential drug panels and their effects on the activity of enzymes, such as molecular motors, and the like. These and other advantages and applications will become more apparent in view of the below description.

In one aspect, the present disclosure provides a method of characterizing a protein in a nanopore system. In this method, the protein is physically associated with a polymer. The method comprises the steps of: (a) applying an electrical potential between the first conductive liquid medium and the second conductive liquid medium of the nanopore system to cause the polymer to interact with the nanopore tunnel; (b) measuring an ion current through the nanopore during the interaction of the polymer with the nanopore tunnel to provide a current pattern; (c) determining a position and/or movement of at least one polymer subunit in the nanopore tunnel from the current pattern; and (d) associating the position and/or movement of the at least one polymer subunit with a characteristic of the protein.

Various aspects of nanopore systems encompassed by the present disclosure are described in more detail below. Generally described, the nanopore system comprises a nanopore disposed in a membrane that separates a first conductive liquid medium from a second conductive liquid medium. The nanopore generally forms an interior tunnel that provides liquid communication between the first conductive liquid medium and the second conductive liquid medium. In the present aspect, the protein is disposed in the first conductive liquid medium and is physically associated with the polymer.

As used herein, the term "physically associated" can refer to a covalent bond to provide a permanent or static association between the protein and the polymer. Alternatively, the term can refer to a non-covalent bond or association between the protein and the polymer. This encompasses embodiments where the protein can have a dynamic physical association with the polymer, such as in the case of many molecular motor enzymes that can contact and apply force to polymer molecules (e.g., nucleic acids) and may move along the length of the polymer in a dynamic movement.

In this method, at least one dimension of the protein exceeds a diameter of the nanopore tunnel. Accordingly, any movement of the associated polymer into the interior space of the nanopore does not result in the passage of the protein itself through the nanopore. Instead, the protein is merely pulled into contact with the outer rim entrance of the nanopore and comes to rest at the outer rim of the nanopore with no further progression towards the opposite side of the membrane. Thus, the protein provides an anchor, whether dynamic or substantially static, to the polymer, that provides resistance to further movement of the polymer into (and possibly through) the nanopore. Thus, by virtue of the protein's position of the protein at the outer rim entrance of the nanopore, the protein's association with the polymer results in a controlled rate of polymer movement (or a substantial prevention of further movement) into or through the nanopore.

The protein is the target analyte for the present disclosure. It will be appreciated that the present disclosure can be widely applied to any target protein of interest for a wide variety of assays. Thus, the present disclosure is not limited to a particular target protein-type. The two limitations are that the protein must have at least one dimension that exceeds an internal diameter of the nanopore to prevent passage of the protein through the nanopore (described above) and that the protein must be capable or amenable to a physical association to the polymer. It will be appreciated that the protein can be any naturally occurring protein, any modified (e.g., engineered) protein, including mutated or fusion proteins. Several categories of potential proteins will be described, although it is noted that these descriptions are merely for illustration purposes and are not intended to be limiting.

In some embodiments, the protein is an enzyme. Broadly defined, and enzyme is a polypeptide macromolecule that, when properly folded into a tertiary structure, can perform work such as catalyze a reaction.

In some embodiments, the enzyme is a molecular motor. A "molecular motor" is broadly defined as a protein, such as an enzyme, that interacts with a particular polymer, such as a nucleic acid. In some embodiments, the interaction involves some force applied to the polymer. In a natural situation, the force might result in the attachment of the molecular motor to the polymer, movement of the molecular motor along the polymer, or a change in conformation or shape of the polymer. The force can result in the manipulation of the polymer, such as causing the movement of the polymer in the nanopore system. The molecular motor can be active, i.e., using energy such as ATP to move or interact with the polymer. Such molecular motors can encompass moieties that can move the polymer against the force direction applied by the voltage cross the nanopore. Alternatively, the molecular motor can be passive, i.e., not using energy to move or interact with the polymer. The present disclosure is useful to characterize the nature of the association between the molecular motor and the particular polymer. For example, many molecular motors move along a nucleic acid strand in discrete and repetitive steps. Such molecular motors, when immobilized against the outer rim entrance of the nanopore, facilitate movement of the nucleic acid in discrete steps through the nanopore in a stepwise fashion where the nucleic acid progresses in discrete movements of a relatively consistent length, akin to a ratchet or queuing motion. Some molecular motors, such as phi29 DNA polymerase (DNAP), move the nucleic acid polymers in single measurable nucleotides steps through the nanopore. However, it will be appreciated that other molecular motors are useful for moving the nucleic acid polymers in steps that are less than a single nucleotide length. Yet other molecular motors are useful for moving the nucleic acid polymers in steps that are more than a single nucleotide in length.

The present method can be used to measure characteristics such as the distance of each movement at a sub-Angstrom resolution by monitoring the resultant movement of the polymer through the nanopore. The method can also be used to characterize the energy requirements of the molecular motor action, by adjusting the availability of chemical energy (such as the concentration of ATP). As another example, the putative co-factors, agonist, antagonist, or any other potential reaction condition can be tested to ascertain the changes conferred on the monitored movement of the polymer through the nanopore. As yet another example, the method can be applied to characterize the rate of the polymer movement through the pore facilitated by the protein in any particular reaction condition or environment. Moreover, molecular motors often commit mistakes wherein the molecular motor skips a step or backs up and repeats a movement step. Such skips or toggles can be detected in the current patterns. See PCT/US2014/059360, incorporated herein by reference in its entirety.

Illustrative, nonlimiting examples of such molecular motors are provided below.

The molecular motor can be a naturally occurring enzyme, an engineered or mutated enzyme, or otherwise derived from an enzyme. In some embodiments, the molecular motor is modified to remove a particular function from the enzyme, but preserves the ability of the molecular motor to associate with the polymer analyte (e.g., nucleic acid) and facilitate its movement within the nanopore. In some embodiments, the enzyme is or is derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme maybe any of those disclosed in International Publication No. WO 2010/1086603, incorporated herein by reference in its entirety.

In some embodiments, the enzyme is a translocase, a polymerase, a helicase, an exonuclease, or topoisomerase, and the like.

Many exemplary exonucleases are generally described in WO 2010/1086603, incorporated herein by reference in its entirety. Other examples are exonucleases, which can include exonuclease I, exonuclease III, lambda exonuclease, or a variant or homolog thereof. For any aspect herein, homologs, derivatives, and other variant proteins, as described herein, can preferably be at least 50% homologous to the reference protein based on amino acid sequence identity. More preferably, the variant polypeptide may be at least 55%, at least 60%, at least 65%, at least 70%, at least 75%, at least 80%, at least 85%, at least 90% and more preferably at least 95%, 97%, or 99% homologous based on amino acid identity to the reference protein, or any range derivable therein. Homology can be determined by any method accepted in the art. Thus, homologs or variants can possess sequence and structural modifications. The present disclosure can be useful to determine or otherwise characterize the functional similarities and/or differences that result from the indicated differences. While exonucleases often contain enzymatic functions for excising portions of the nucleic acids, such enzymes can be modified to ablate such nuclease function while preserving the ability to bind and move the nucleic acid polymer.

Exemplary helicases that can be target proteins are generally described in WO 2014/013260 and WO 2013/057495, each reference incorporated herein by reference in its entirety, and can include a hel308 helicase, a RecD helicase, a Tral helicase, a Tral subgroup helicase, an XPD helicases, or a variant or homolog thereof.

Exemplary polymerases that can be target proteins include DNA polymerases such as phi29 DNA polymerase (sometimes referred to as phi29 DNAP), Klenow fragment, or a variant or homolog thereof.

Exemplary topoisomerases can include a gyrase, or a variant or homolog thereof.

Other target proteins include viral packaging motors, or any other viral or pathogen enzyme that facilitates invasion, replication, or other pathogenic function by the pathogen.

Yet other exemplary target proteins include Brownian motors, Brownian ratchet ribosome, myosin, kinesin, and the like, as are known in the art.

As indicated above, the present method can also be applied to characterize conformational states of proteins. In this regard, the wildtype target protein need not have any affinity for associating with the polymer. Instead the polymer can be covalently coupled to the protein according to any standard and commonly recognized technique in the art. In this context, the conformational state can be characterized by the position of a particular polymer subunit within the nanopore. This is indicative of the distance between the protein and the particular polymer subunit, or indeed the constriction zone of the nanopore. Any change in this conformational state can result in minute changes in this distance, which are detectable in this system. Thus, multiple proteins can be compared (using the same polymer-type attached in the same manner, i.e., to the same amino acid residue of the protein). This permits mutational studies to characterize the conformational changes that result from the introduction of one or more mutations into a protein sequence. Additionally, a protein may be a natural or fusion protein that comprises two or more domains that mutually interact, thus causing a conformational change. The various parameters of this interaction can be inferred by measuring the movement of the polymer in the nanopore, such as the frequency, duration, and quality (inferred by distance of polymer movement).

In the present method, the application of an electrical potential across the membrane (i.e., between the first conductive liquid medium and the second conductive liquid medium) causes the polymer to interact with the nanopore tunnel. Typically, the polymer analyte (e.g., nucleic acid) interacts with the nanopore tunnel in a linear fashion where the polymer is extended linearly along the axis of the nanopore tunnel. In some embodiments, this axis is transverse to the membrane. The term "interact," when used with respect to the nanopore tunnel, indicates that the polymer moves into at least an interior portion of the nanopore to an extent that the presence of the polymer influences the measurable ion current that runs through the nanopore tunnel. As described in more detail below, many nanopores have a "constriction" or "constriction zone," which is an area of the internal tunnel that has the smallest diameter and, thus, where the current is most likely to be differentially affected by the presence of varying polymer structures.

The polymers encompassed by this disclosure can be any polymer capable of 1) an association with the target protein, and 2) an interaction with the interior tunnel of the nanopore such that an ionic current through the nanopore can be measurably affected by the structure of the polymer. In practice, the polymer serves as a yardstick to characterize distance between the protein, to which the polymer is attached and is situated at the outer rim opening of the nanopore, and the region within the tunnel where the presence of the polymer can affect the measurable current within the pore (often referred to as the "constriction zone"). Measurement of this distance is possible because the position of polymer subunits can be monitored within the nanopore due to the variations in the current pattern observed during the assay. The determination of the position within a nanopore of a polymer nucleotide subunit in a nucleic acid polymer is described in more detail in PCT/US2014/059360, incorporated herein by reference in its entirety.

As used herein, a "polymer" refers to any macromolecule that comprises two or more linear units (also known as a "mers" or "subunits"), where each subunit may be the same or different. Non-limiting examples of polymers encompassed by the present disclosure include nucleic acids, peptides, and proteins, as well as a variety of hydrocarbon polymers (e.g., polyethylene, polystyrene) and functionalized hydrocarbon polymers, wherein the backbone of the polymer comprises a carbon chain (e.g., polyvinyl chloride, polymethacrylates). The term "polymer" can also include copolymers, block copolymers, and branched polymers such as star polymers and dendrimers.

In any embodiment, there is no requirement that the polymer sequence be known a priori, or even be decipherable from the current patterns produced in the nanopore system. Instead, among the polymer subunits a measureable change in the ion current can be produced and the position of the structural variation in the polymer be ascertainable relative to the nanopore tunnel and/or the position of the protein at the outer entrance rim. Accordingly, in some embodiments the polymer (e.g., nucleic acid) is not a homopolymer.

The term "nucleic acid" refers to any polymer molecule that comprises multiple nucleotide subunits (i.e., a polynucleotide). Nucleic acids encompassed by the present disclosure can include deoxyribonucleotide polymer (DNA), ribonucleotide polymer (RNA), cDNA or a synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains, or any combination thereof. The nucleic acids can be in either single- or double-stranded form, or comprise both single and double stranded portions. Typically cDNA, RNA, GNA, TNA, or LNA are single stranded. DNA can be either double stranded (dsDNA) or single stranded (ssDNA).

Nucleotide subunits of the nucleic acid polymers can be naturally occurring or artificial or modified. A nucleotide typically contains a nucleobase, a sugar, and at least one phosphate group. The nucleobase is typically heterocyclic. Suitable nucleobases include purines and pyrimidines and more specifically adenine (A), guanine (G), thymine (T) (or typically in RNA, uracil (U) instead of thymine (T)), and cytosine (C). The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate, or triphosphate. These are generally referred to herein as nucleotides or nucleotide residues to indicate the subunit. Without specific identification, the general terms nucleotides, nucleotide residues, and the like, are not intended to imply any specific structure or identity. The nucleotides can also be synthetic or modified. For example, the nucleotide can be labeled or modified to act as a marker with a distinct signal. Furthermore, before the application of the electric potential, modifications can be applied to the nucleic acid that selectively affects the structure of a limited nucleotide-type to enhance the differentiation of the resulting signal for the targeted residue (subunit). For example, see International Application No. PCT/US2014/53754, incorporated herein by reference in its entirety. One particular advantageous strategy for the practice of the present disclosure is to incorporate a nucleic acid residue with a missing base structure, for example, an abasic unit or spacer in the polynucleotide. This is particularly advantageous because abasic residues have been observed to result in a marked current spike (i.e., sharp increase in current) when positioned within the constriction zone. Accordingly, the specific position of the abasic residue (or residues) can be readily monitored with little risk of signal confusion. This provides a useful signal for monitoring the position and movement of the abasic residue through the nanopore, as permitted or influenced by the associated protein.

The present disclosure also encompasses the use of polypeptides as the polymer. A "polypeptide" is a macromolecule of multiple amino acids linked by peptide (amide) bonds. As used herein, an "amino acid" refers to any of the naturally occurring amino acids found in proteins, D-stereoisomers of the naturally occurring amino acids (e.g., D-threonine), unnatural amino acids, and chemically modified amino acids. Each of these types of amino acids is not mutually exclusive. α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine).

The following abbreviations are used for the 20 naturally occurring canonical amino acids: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unnatural amino acids (that is, those that are not naturally found in proteins) are also known in the art, as set forth in, for example, *Mol. Cell. Biol.*, 9:2574 (1989); *J. Amer. Chem. Soc.*, 112:4011-4030 (1990); *J. Amer. Chem. Soc.*, 56:1280-1283 (1991); *J. Amer. Chem. Soc.*, 113:9276-9286 (1991); and all references cited therein. β- and γ-amino acids are known in the art and are also contemplated herein as unnatural amino acids.

As used herein, a "chemically modified amino acid" refers to an amino acid whose side chain has been chemically modified. For example, a side chain may be modified to comprise a signaling moiety, such as a fluorophore or a radiolabel. A side chain may be modified to comprise a new functional group, such as a thiol, carboxylic acid, or amino group. Post-translationally modified amino acids are also included in the definition of chemically modified amino acids.

As described above, the current patterns produced in the described systems that contain a target protein associated with a polymer can be used to ascertain a characteristic of the protein. This is enabled by the discovery that such nanopore systems can permit a highly resolved inference of the position of a single polymer subunit within the nanopore, and changes in that position over minute ranges of time. This analysis is based on a preliminary force spectroscopy investigation on single-stranded DNA (ssDNA) within a nanopore. The inventors previously found that an anchored DNA analyte stretches within the constriction zone of MspA with increasing force, as applied with an increased electric potential in the nanopore system. By varying electric potential in the nanopore system and simultaneously monitoring the resulting current, the stretching of the DNA within the nanopore was characterized at angstrom-level precision. Using a freely jointed chain model to assess the stretching, the relative positions of the nucleotides were characterized during the stretch events and ascertaining the relative contribution of Brownian motion to the sensitivity of the nanopore system to multiple nucleotides was established.

Due to the insight from the spring modeling analysis, the positions of the nucleotides can be calculated at any point during the DNA interaction with the nanopore tunnel. Thus the current pattern is amenable to analysis that identifies any current pattern as corresponding to a segment of the nucleic acid residing in the constriction zone of the nanopore associated with the application of an electrical potential. Thus, in some embodiments, the conversion of the current-potential curve into a current-nucleic acid distance curve is accomplished by application of a spring-based model. In some embodiments, the model is a model of spring with a linear restoring force. In some embodiments, the model is a non-linear restoring force as in a freely jointed chain (FJC) model or modified freely jointed chain (FJC) model, as described in more detail below. Other appropriate models can be applied according to the skill in the art. See PCT/US2014/059360, incorporated herein by reference in its entirety.

In another aspect, the present disclosure provides a method of characterizing a protein in a nanopore system. As above, the protein in this aspect is physically associated with a polymer. The method of this aspect specifically comprises: (a) applying an electrical potential between the first conductive liquid medium and the second conductive liquid medium to cause the polymer to interact with the nanopore tunnel; (b) measuring an ion current through the nanopore during the interaction of the polymer with the nanopore tunnel to provide a first current pattern; (c) comparing the first current pattern to a reference current pattern; (d) determining a change in position and/or movement of at least one polymer subunit in the nanopore tunnel from the position and/or movement of at least one polymer subunit in the nanopore tunnel determined from the reference current pattern; and (e) associating the change in position and/or movement of the at least one polymer subunit in the nanopore tunnel with a characteristic of the enzyme.

Various aspects of nanopore systems encompassed by the present disclosure are described in more detail below. Generally described, the nanopore system comprises a nanopore disposed in a membrane that separates a first conductive liquid medium from a second conductive liquid medium, wherein the nanopore comprises a tunnel that provides liquid communication between the first conductive liquid medium and the second conductive liquid medium, and wherein the protein is physically associated with a polymer in the first conductive liquid medium.

As described above, the at least one dimension of the protein exceeds a diameter of the nanopore tunnel.

The present parameters and features of this method are as described in context of the method above. In this aspect, the method involved comparing the first current pattern to a reference current pattern. Thus, this method is applicable to an experimental setup to ascertain the effect of one or more changes in conditions of a reaction. The effect is ideally attributable to a characteristic or effect on the target protein. Thus, when a difference is detected between the polymer positions, as reflected in the first current pattern and a reference current pattern, the difference can be attributed to a change in the assay conditions that produced each respective current pattern. Thus, the conditions of the assay in the recited nanopore system comprises a perturbation, or difference, compared to the conditions used to generate the reference current pattern.

In some embodiments, the difference can be the addition or removal of a putative protein agonist, antagonist, or co-factor. In such embodiments, the method can be employed to test one or more of a panel of potential factors suspected of influencing a protein. For example, factors suspected of potentially specifically inhibiting a viral helicase can be tested and the ability of the helicase to move along DNA characterized by measuring the rate of movement of the DNA polymer in the nanopore.

In other embodiments, mutations in the protein that are suspected of altering the interaction with nucleic acid polymers can be tested by characterizing the speed, frequency, or character of nucleic acid movements.

In other embodiments, the difference can be a difference in reaction conditions, such as a difference in the presence of a co-factor, or an alteration in the co-factor. In other embodiments, the difference can be a change in the concentration (either higher or lower) of components like ATP, and the like.

The first and reference current patterns can be generated in the same or different nanopore system setup with the same or different protein and associated polymer. In some embodiments, the system, protein, and polymer are substantial duplicates but for the particular introduced perturbation. In some embodiments, the method comprises generating the reference current pattern. In some embodiments, the reference current pattern is generated before or after the first current pattern is generated, wherein the patterns are each generated before or after the introduction of the perturbation, respectively. In some embodiments, the perturbation is introduced into the system and the effect on the conformation of the protein is ascertained by ascertaining the changes in polymer (or polymer subunit) position or movement within the nanopore.

Various aspects of the nanopore systems as employed in the present disclosure are described below.

Nanopore-based analysis methods have previously been investigated for the characterization of analytes that are passed through the nanopore. The systems permit the passing of a polymeric molecule, for example, single-stranded DNA ("ssDNA"), through a nanoscopic opening while providing a signal, such as an electrical signal, that is influenced by the physical properties of the polymer subunits that reside in the close physical space of the nanopore tunnel at any given time. The nanopore optimally has a size or three-dimensional configuration that allows the polymer to pass only in a sequential, single file order. Under theoretically optimal conditions, the polymer molecule passes through the nanopore at a rate such that the passage of each discrete monomeric subunit of the polymer can be correlated with the monitored signal. Differences in the chemical and physical properties of each monomeric subunit that makes up the polymer, for example, the nucleotides that compose an ssDNA, result in characteristic electrical signals that can identify each monomeric subunit as it passes through the nanopore. Nanopores, such as solid state nanopores and protein nanopores held within lipid bilayer membranes, have been heretofore used for analysis of DNA, RNA, and polypeptides and, thus, provide an advantageous platform for a robust analysis of polymer position and movement as a reflection on an associated protein.

A "nanopore" specifically refers to a pore typically having a size of the order of nanometres that allows the passage of analyte polymers (such as nucleic acids) therethrough. Typically, nanopores encompassed by the present disclosure have an opening with a diameter at its most narrow point of about 0.3 nm to about 2 nm. Nanopores useful in the present disclosure include any pore capable of permitting the linear translocation of the analyte polymer from one side to the other at a velocity amenable to monitoring techniques, such as techniques to detect current fluctuations.

Nanopores can be biological nanopores (e.g., proteinaceous nanopores), solid state nanopores, hybrid solid state protein nanopores, a biologically adapted solid state nanopore, a DNA origami nanopore, and the like.

In some embodiments, the nanopore comprises a protein, such as alpha-hemolysin, anthrax toxin and leukocidins, and outer membrane proteins/porins of bacteria such as *Mycobacterium smegmatis* porins (Msp), including MspA, outer membrane porins such as OmpF, OmpG, OmpATb, and the like, outer membrane phospholipase A and *Neisseria* autotransporter lipoprotein (NaIP), and lysenin, as described in U.S. Publication No. US2012/0055792, International PCT Publication Nos. WO2011/106459, WO2011/106456, WO2013/153359, and Manrao et al., "Reading DNA at single-nucleotide resolution with a mutant MspA nanopore and phi29 DNA polymerase," *Nat. Biotechnol.* 30:349-353 (2012), each of which is incorporated herein by reference in its entirety. Nanopores can also include alpha-helix bundle pores that comprise a barrel or channel that is formed from a-helices. Suitable a-helix bundle pores include, but are not limited to, inner membrane proteins and an outer membrane proteins, such as WZA and ClyA toxin. In one embodiment, the protein nanopore is a heteroligomeric cationic selective channel from *Nocardia faricinica* formed by NfpA and NfpB subunits. The nanopore can also be a homolog or derivative of any nanopore illustrated above. A "homolog," as used herein, is a gene or protein from another species that has a similar structure and evolutionary origin. By way of an example, homologs of wild-type MspA, such as MppA, PorM1, PorM2, and Mmcs4296, can serve as the nanopore in the present invention. Protein nanopores have the advantage that, as biomolecules, they self-assemble and are essentially identical to one another. In addition, it is possible to genetically engineer protein nanopores, thus creating a "derivative" of a nanopore, such as those illustrated above, that possesses various attributes. Such derivatives can result from substituting amino acid residues for amino acids with different charges, from the creation of a fusion protein (e.g., an enzyme+alpha-hemolysin). Thus, the protein nanopores can be wild-type or can be modified to contain at least one amino acid substitution, deletion, or addition. In some embodiments, the at least one amino acid substitution, deletion, or addition results in a different net charge of the nanopore. In some embodiments, the difference in net charge increases the difference of net charge as compared to the first charged moiety of the polymer analyte. For example, if the first charged moiety has a net negative charge, the at least one amino acid substitution, deletion, or addition results in a nanopore that is less negatively charged. In some cases, the resulting net charge is negative (but less so), is neutral (where it was previously negative), is positive (where it was previously negative or neutral), or is more positive (where it was previously positive but less so). In some embodiments, the alteration of charges in the nanopore entrance rim or within the interior of the tunnel and/or constriction facilitate the entrance and interaction of the polymer with the nanopore tunnel.

In some embodiments, the nanopores can include or comprise DNA-based structures, such as generated by DNA origami techniques. For descriptions of DNA origami-based nanopores for analyte detection, see PCT Publication No. WO2013/083983, incorporated herein by reference.

In some embodiments, the nanopore is an MspA or homolog or derivative thereof. MspA is formed from multiple monomers. The pore may be homomonomeric or heteromonomeric, where one or more of the monomers contains a modification or difference from the others in the assembled nanopore. Descriptions of modifications to MspA nanopores have been described, see U.S. Publication No. 2012/0055792, incorporated herein by reference in its entirety. Briefly described, MspA nanopores can be modified with amino acid substitutions to result in a MspA mutant with a mutation at position 93, a mutation at position 90, position 91, or both positions 90 and 91, and optionally one or more mutations at any of the following amino acid positions: 88, 105, 108, 118, 134, or 139, with reference to the wild type amino acid sequence. In one specific embodiment, the MspA contains the mutations D90N/D91N/D93N, with reference to the wild type sequence positions (referred to therein as "M1MspA" or "M1-NNN"). In another embodiment, the MspA contains the mutations D90N/D91N/D93N/D118R/D134R/E139K, with reference to the wild type sequence positions (referred to therein as "M2MspA"). See U.S. Publication No. 2012/0055792. Such mutations can result in a MspA nanopore that comprises a vestibule having a length from about 2 to about 9 nm and a diameter from about 2 to about 6 nm, and a constriction zone having a length from about 0.3 to about 3 nm and a diameter from about 0.3 to about 3 nm, wherein the vestibule and constriction zone together define a tunnel. Furthermore, the amino acid substitutions described in these examples provide a greater net positive charge in the vestibule of the nanopore, further enhancing the energetic favorability of interacting with a negatively charged polymer analyte end.

Some nanopores, such as MspA protein nanopores, can comprise a variably shaped tunnel component through which the polymer analyte moves. For example, an exemplary embodiment where MspA is disposed in a lipid bilayer membrane. The MspA nanopore comprises an outer entrance rim region that contacts the illustrated enzyme. The widest interior section of the tunnel is often referred to as the vestibule. The narrowest portion of the interior tunnel is referred to as the constriction zone. The vestibule and a constriction zone together form the tunnel. A "vestibule" in MspA is a cone-shaped portion of the interior of the nanopore whose diameter generally decreases from one end to the other along a central axis, where the narrowest portion of the vestibule is connected to the constriction zone. Stated otherwise, the vestibule of MspA may generally be visualized as "goblet-shaped." Because the vestibule is goblet-shaped, the diameter changes along the path of a central axis, where the diameter is larger at one end than the opposite end. The diameter may range from about 2 nm to about 6 nm. Optionally, the diameter is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. The length of the central axis may range from about 2 nm to about 6 nm. Optionally, the length is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. When referring to "diameter" herein, one can determine a diameter by measuring center-to-center distances or atomic surface-to-surface distances.

Figure 2A:
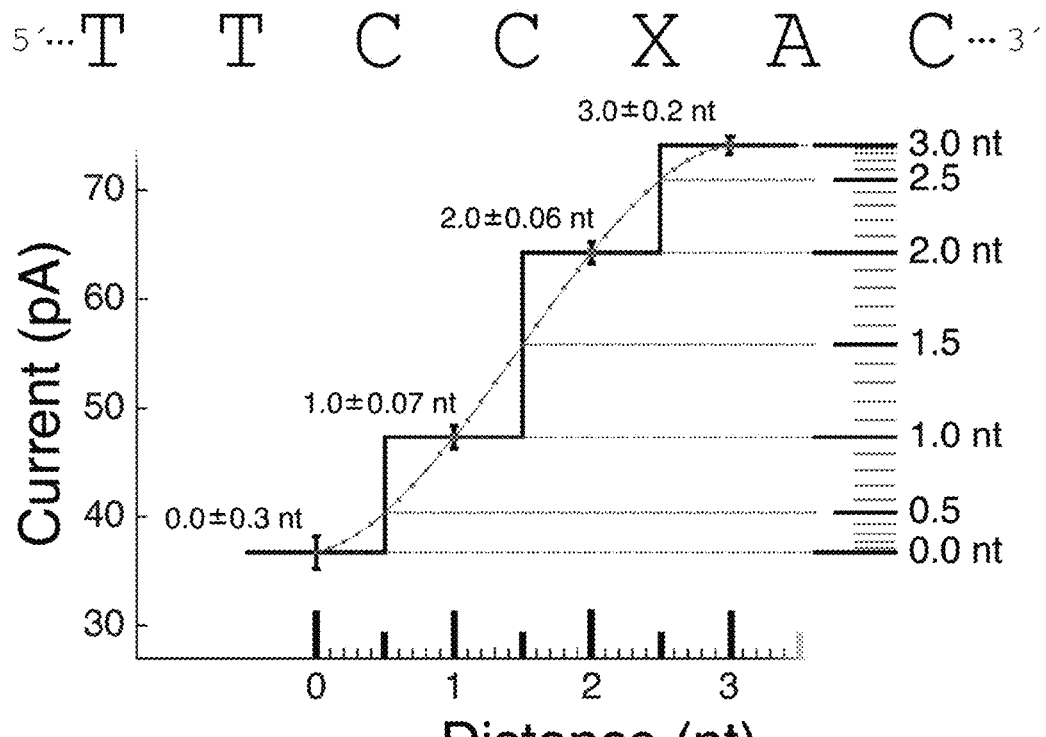
FIGS. 2A-2F illustrate the process and sensitivity of the PINT system by characterizing at a small scale the DNA movement in the nanopore for protein analysis.
Figure 2B:
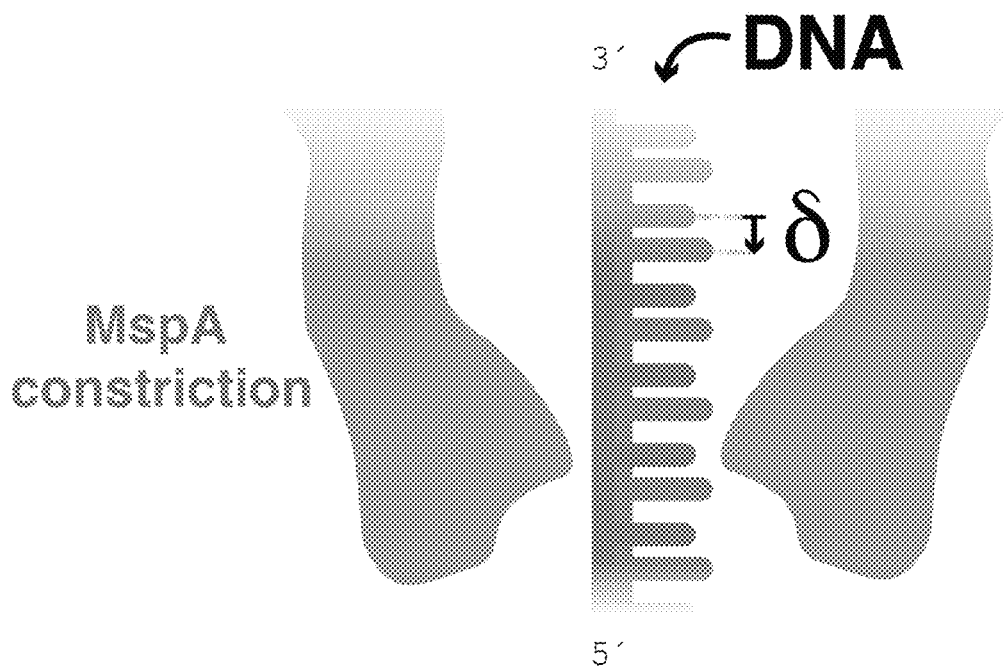
Figure 2C:
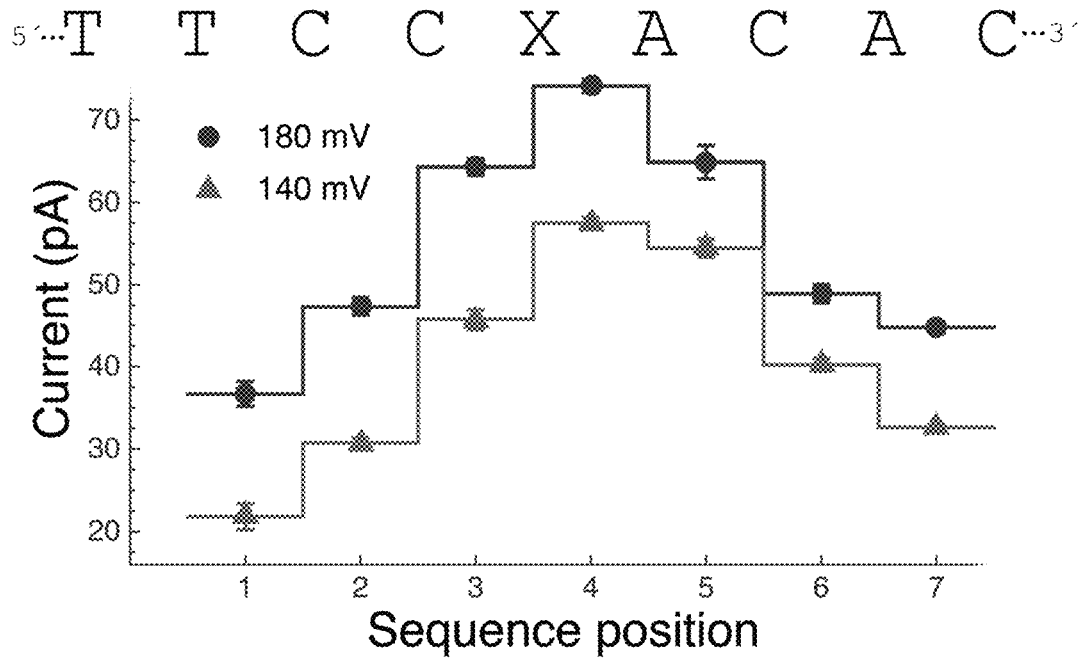
Figure 2D:
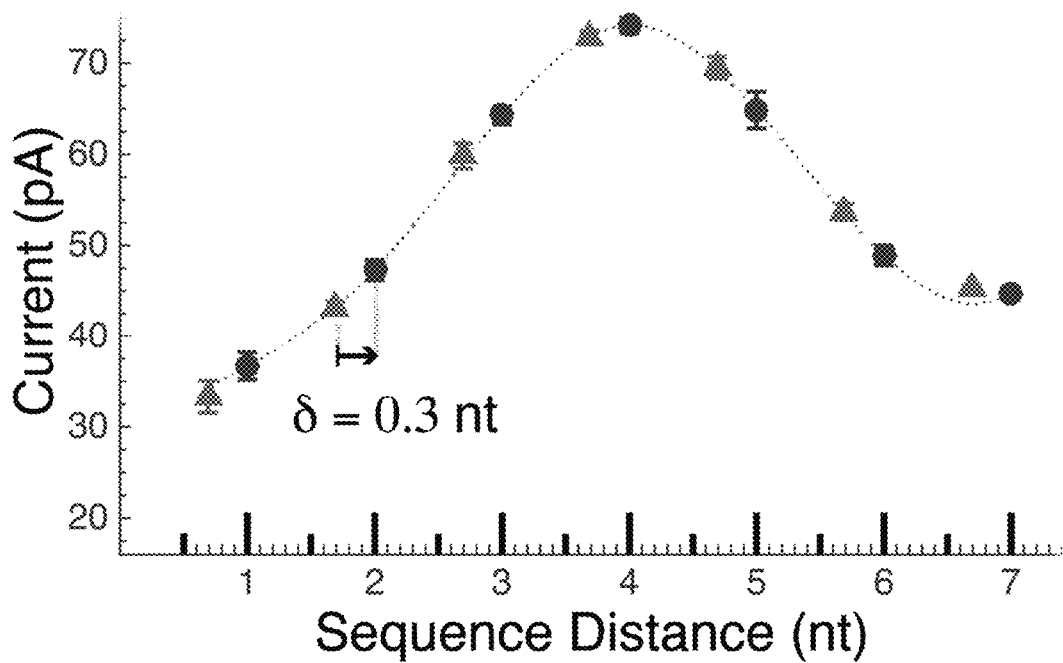
Figure 2E:
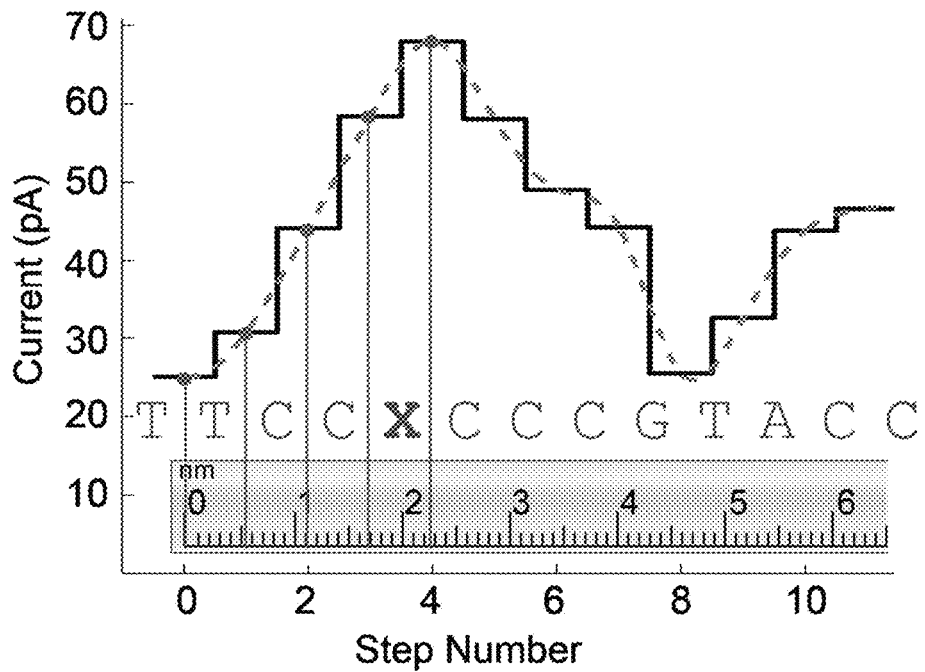
Figure 2F:
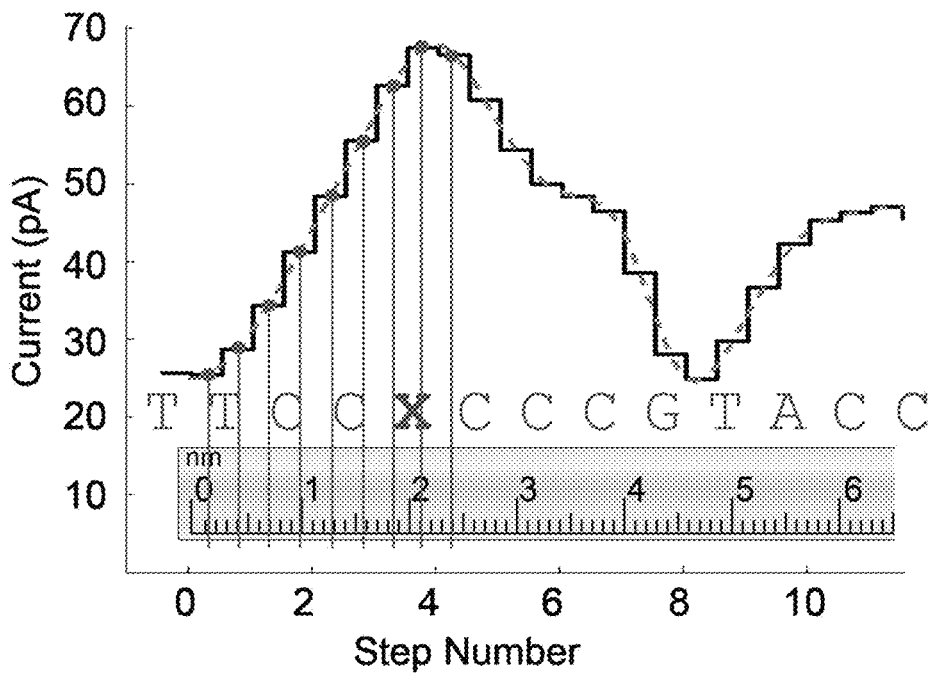
Figure 3A:
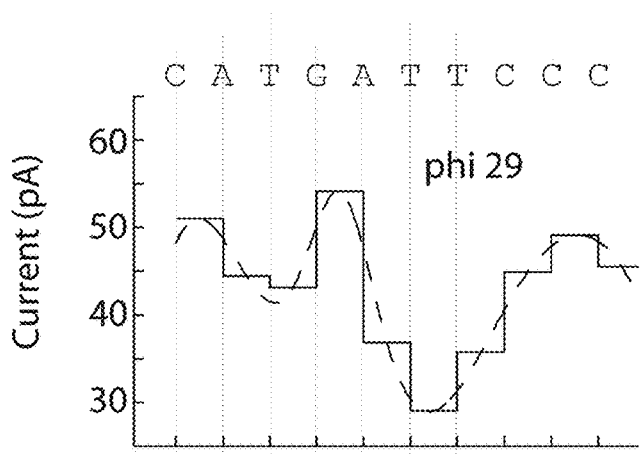
FIGS. 3A-3G illustrate the nanopore-based analysis of DNA translocation steps controlled by hel308. The DNA sequence in FIG. 3A is set forth as SEQ ID NO:4.
Figure 3B:
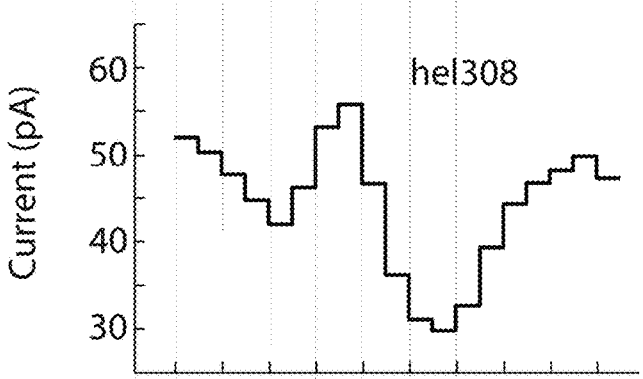
Figure 3C:
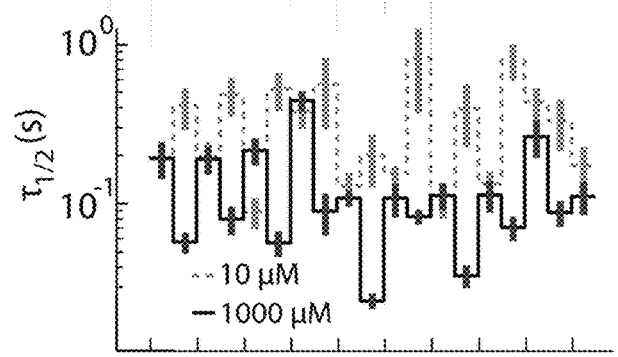
Figure 3D:
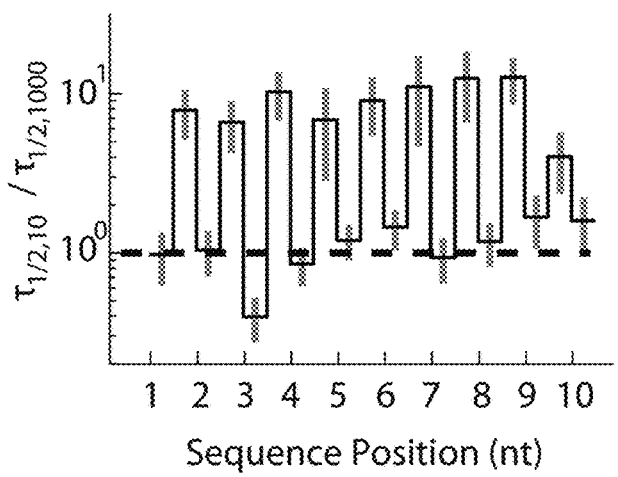
Figure 3E:
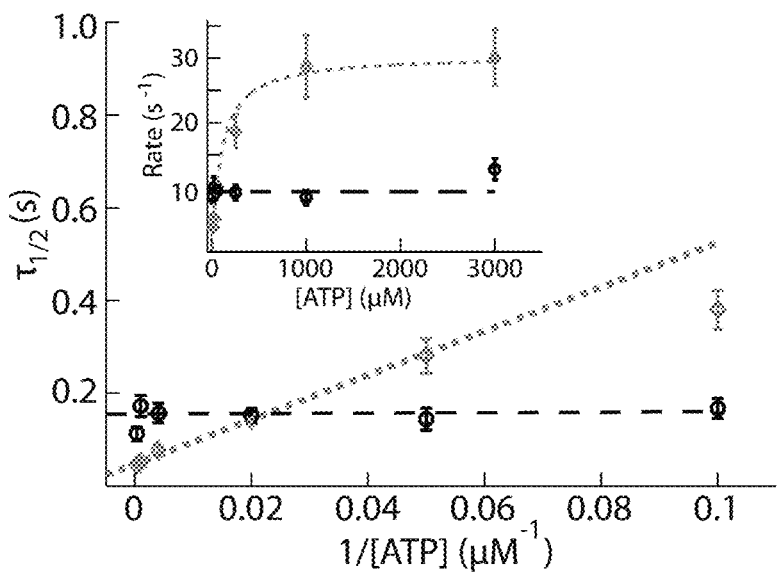
Figure 3F:
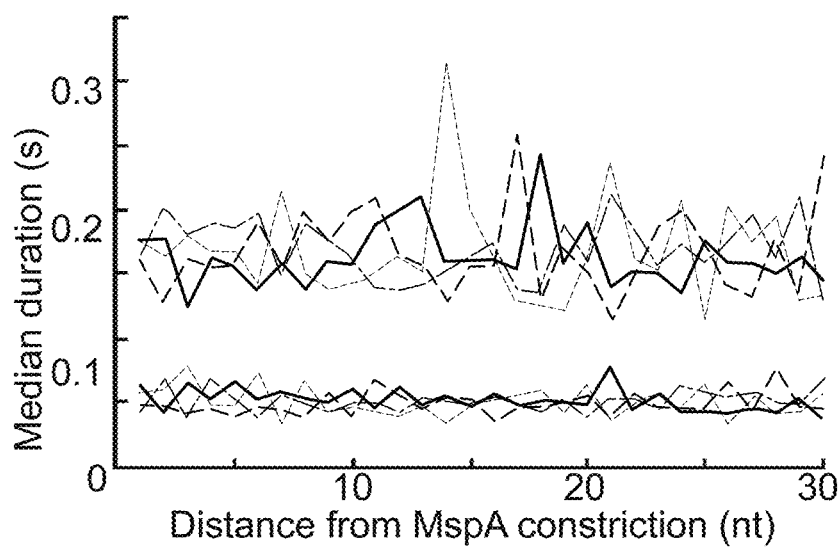
Figure 3G:
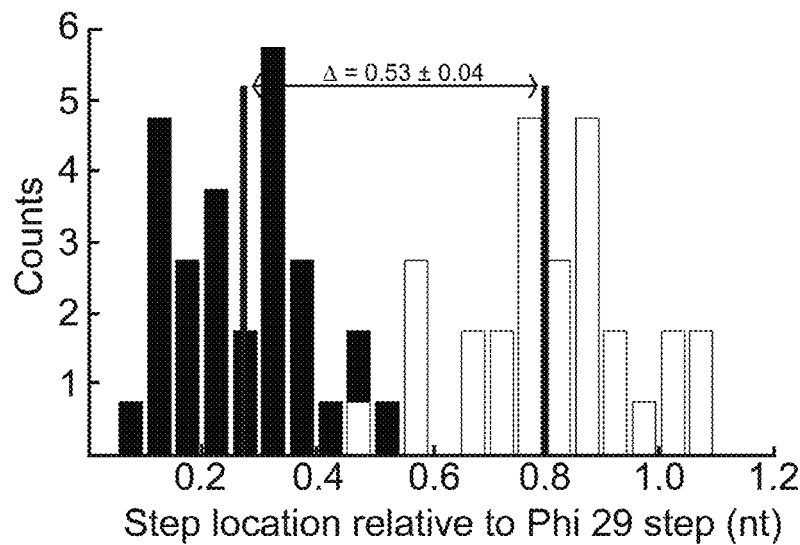

The term "constriction zone" generally refers to the narrowest portion of the tunnel of the nanopore, in terms of diameter, that is connected to the vestibule. The length of the constriction zone can range, for example, from about 0.3 nm to about 20 nm. Optionally, the length is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. The diameter of the constriction zone can range from about 0.3 nm to about 2 nm. Optionally, the diameter is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. In other embodiment, such as those incorporating solid state pores, the range of dimension (length or diameter) can extend up to about 20 nm. For example, the constriction zone of a solid state nanopore is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, or 20 nm, or any range derivable therein. Larger dimension in such nanopores can be preferable depending on the polymer used in the method. As described in more detail below, the constriction zone is generally the part of the nanopore structure where the presence of a polymer, such as a nucleic acid, can influence the ionic current from one side of the pore to the other side of the nanopore. FIG. 2B provides an illustrative diagram of a constriction zone that is sensitive to a subsequence of several nucleotides of a polymer. In this example, a specific position within the constriction zone has the highest sensitivity for determining the current through the nanopore, as indicated by the vertical line and an indication of 0 nm displacement. Thus, the nucleotide residing in that position at any time will provide the greatest influence on the current signal and the neighboring nucleotides in the constriction zone have diminished influence on the signal. Accordingly, the dimensions of the nanopore's constriction zone can influence the resolution of the current signal as it relates to the structure (and sequence identity) of the analyte polymer residing therein. In some instances, the term "constriction zone" is used in a functional context based on the obtained resolution of the nanopore and, thus, the term is not necessarily limited by any specific parameter of physical dimension. Thus, a nanopore's functional constriction zone can be optimized by modifying aspects of the nanopore system but without providing for any physical modification to the nanopore itself.

In some embodiments, the nanopore can be a solid state nanopore. A solid-state layer is not of biological origin. In other words, a solid state layer is not derived from or isolated from a biological environment such as an organism or cell, or a synthetically manufactured version of a biologically available structure. Solid state nanopores can be produced as described in U.S. Pat. Nos. 7,258,838 and 7,504,058, incorporated herein by reference in their entireties. Briefly, solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon®, or elastomers such as two-component addition-cure silicone rubber, and glasses. The solid state layer may be formed from graphene. Suitable graphene layers are disclosed in WO 20091035647 and WO 20111046706. Solid state nanopores have the advantage that they are more robust and stable. Furthermore, solid state nanopores can in some cases be multiplexed and batch fabricated in an efficient and cost-effective manner. Finally, they might be combined with micro-electronic fabrication technology. In some embodiments, the nanopore comprises a hybrid protein/solid state nanopore in which a nanopore protein is incorporated into a solid state nanopore. In some embodiments, the nanopore is a biologically adapted solid-state pore.

In some cases, the nanopore is disposed within a membrane, thin film, layer, or bilayer. For example, biological (e.g., proteinaceous) nanopores can be inserted into an amphiphilic layer such as a biological membrane, for example, a lipid bilayer. An amphiphilic layer is a layer formed from amphiphilic molecules, such as phospholipids, which have both hydrophilic and lipophilic properties. The amphiphilic layer can be a monolayer or a bilayer. The amphiphilic layer may be a co-block polymer. Alternatively, a biological pore may be inserted into a solid state layer.

The membrane, thin film, layer, or bilayer typically separates a first conductive liquid medium and a second conductive liquid medium to provide a nonconductive barrier between the first conductive liquid medium and the second conductive liquid medium. The nanopore, thus, provides liquid communication between the first and second conductive liquid media through its internal tunnel. In some embodiments, the pore provides the only liquid communication between the first and second conductive liquid media. The conductive liquid media typically comprises electrolytes or ions that can flow from the first conductive liquid medium to the second conductive liquid medium through the interior of the nanopore. Liquids employable in methods described herein are well-known in the art. Descriptions and examples of such media, including conductive liquid media, are provided in U.S. Pat. No. 7,189,503, for example, which is incorporated herein by reference in its entirety. The first and second liquid media may be the same or different, and either one or both may comprise one or more of a salt, a detergent, or a buffer. Indeed, any liquid media described herein may comprise one or more of a salt, a detergent, or a buffer. Additionally, any liquid medium described herein may comprise a viscosity altering substance or a velocity altering substance.

In some cases, the first and second conductive liquid media located on either side of the nanopore are referred to as being on the cis and trans regions, where the protein analyte and the associated polymer are provided in the cis region. However, it will be appreciated that in some embodiments, the protein analyte to be analyzed and the associated polymer can be provided in the trans region and, upon application of the electrical potential, the polymer enters the nanopore from the trans side of the system. In some cases, the entire length of the polymer does not pass through the pore, but only certain portions or segments of the polymer pass through the nanopore for analysis. The directionality and rate of translocation can be regulated using various mechanisms such as applied voltage or the incorporation of a nanopore in the reverse orientation.

Nanopore systems also incorporate structural elements to measure and/or apply an electrical potential across the nanopore-bearing membrane or film. For example, the system can include a pair of drive electrodes that drive current through the nanopores. Typically, the negative pole is disposed in the cis region and the positive pole is disposed in the trans region. Additionally, the system can include one or more measurement electrodes that measure the current through the nanopore. These can include, for example, a patch-clamp amplifier or a data acquisition device. For example, nanopore systems can include an Axopatch-200B patch-clamp amplifier (Axon Instruments, Union City, CA) to apply voltage across the bilayer and measure the ionic current flowing through the nanopore. For example, in some embodiments, the applied electrical field includes a direct or constant current that is between about 10 mV and about 1 V. In some embodiments that include protein-based nanopores embedded in lipid membranes, the applied current includes a direct or constant current that is between about 10 mV and 300 mV, such as about 10 mV, 20 mV, 30 mV, 40 mV, 50 mV, 60 mV, 70 mV, 80 mV, 90 mV, 100 mV, 110 mV, 120 mV, 130 mV, 140 mV, 150 mV, 160 mV, 170 mV, 180 mV, 190 mV, 200 mV, 210 mV, 220 mV, 230 mV, 240 mV, 250 mV, 260 mV, 270 mV, 280 mV, 290 mV, 300 mV, or any voltage therein. In some embodiments, the applied electrical field is between about 40 mV and about 200 mV. In some embodiments, the applied electrical field includes a direct or constant current that is between about 100 mV and about 200 mV. In some embodiments, the applied electrical direct or constant current field is about 180 mV. In other embodiments where solid state nanopores are used, the applied direct or constant current electrical field can be in a similar range as described, up to as high as 1 V. As will be understood, the voltage range that can be used can depend on the type of nanopore system being used and the desired effect.

Persons of skill in the art will readily appreciate that the reverse electrical potential as the values and ranges described above can also be applied. This may be applicable where a molecular motor is characterized in the context of an electrical field that resists the force applied by the molecular motor on the polymer.

In some embodiments, the electrical potential is not constant, but rather is variable about a reference potential. Such use of variable potential in the context of a nucleic acid polymer can cause stretching of the polymer to provide for more data sampling for each position of the polymer relative to the nanopore. This can be applied to methods involving a molecular motor with a dynamic association with the polymer, or to methods involving covalently coupled polymers that do not move in discrete steps but are rather anchored by the protein. See PCT/US2014/059360, incorporated herein by reference in its entirety.

It is generally noted that the use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. Words such as "about" and "approximately" imply minor variation around the stated value, usually within a standard margin of error, such as within 10% or 5% of the stated value.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

The following describes an illustrative use of the disclosed method to characterize the association between the molecular motor, helicase hel308, with DNA at a sub-Angstrom level of resolution.

The embodiments of the invention in which an exclusive property or privilege is claimed are defined as follows:

1. A method of identifying a molecule/drug effective in modulating the activity and/or conformation state of an enzyme in a nanopore system comprising a nanopore disposed in a membrane that separates a first conductive liquid medium from a second conductive liquid medium, wherein the nanopore comprises a tunnel that provides liquid communication between the first conductive liquid medium and the second conductive liquid medium, wherein the molecule/drug is present in the first conductive medium, and wherein the enzyme is physically associated with a polynucleotide in the first conductive liquid medium, the method comprising:
   (a) applying an electrical potential between the first conductive liquid medium and the second conductive liquid medium and causing the polynucleotide to interact with the nanopore tunnel, wherein the enzyme is unable to pass through the nanopore tunnel;
   (b) measuring an ion current through the nanopore during the interaction of the polynucleotide with the nanopore tunnel to provide a first current pattern;
   (c) comparing the first current pattern to a reference current pattern;
   (d) determining a change in position and/or movement of at least one polynucleotide subunit in the nanopore tunnel from the position and/or movement of at least one polynucleotide subunit in the nanopore tunnel determined from the reference current pattern; and
   (e) associating the change in position and/or movement of the at least one polynucleotide subunit to identify the molecule/drug effective in modulating the activity or the conformation state of the enzyme,
   wherein the reference current pattern is generated in the absence of the molecule/drug or in presence of a different concentration of the molecule/drug from the concentration used to generate the first current pattern in the first conductive medium.

2. The method of claim 1, wherein the polynucleotide is a DNA, RNA, a peptide nucleic acid ("PNA"), or a combination thereof.

3. The method of claim 2, wherein the nucleic acid comprises an abasic residue.

4. The method of claim 1, wherein the enzyme is a molecular motor.

5. The method of claim 4, wherein the molecular motor is a translocase, a polymerase, a helicase, an exonuclease, a viral packaging motor, or a topoisomerase.

6. The method of claim 4, wherein the movement of the at least one polynucleotide subunit is associated with a length of a discrete translocation step of the polynucleotide within the nanopore tunnel that is conferred by the molecular motor.

7. The method of claim 4, wherein the movement of the at least one polynucleotide subunit is associated with a temporal duration of a discrete translocation step of the polynucleotide within the nanopore tunnel that is conferred by the molecular motor.

8. The method of claim 1, wherein the enzyme is a Brownian motor, Brownian ratchet ribosome, myosin, or kinesin.

9. The method of claim 1, wherein the enzyme is a mutant enzyme.

10. The method of claim 1, wherein the enzyme comprises two or more domains capable of mutual interaction.

11. The method of claim 1, wherein the enzyme is covalently coupled to the polynucleotide.

12. The method of claim 1, wherein the position of the at least one polynucleotide subunit is associated with a conformational state of the enzyme.

13. The method of claim 1, wherein the nanopore is a solid-state nanopore, a protein nanopore, a hybrid solid state-protein nanopore, a biologically adapted solid-state nanopore, or a DNA origami nanopore.

14. The method of claim 13, wherein the protein nanopore is alpha-hemolysin, leukocidin, *Mycobacterium smegmatis* porin A (MspA), outer membrane porin F (OmpF), outer membrane porin G (OmpG), outer membrane phospholipase A, *Neisseria* autotransporter lipoprotein (NalP), WZA, *Nocardia farcinica* NfpA/NfpB cationic selective channel, lysenin or a homolog or variant thereof.

15. The method of claim 1, wherein the molecule/drug is a putative agonist, antagonist, or co-factor for the enzyme.

16. The method of claim 15, wherein the nanopore system comprises a difference from the nanopore system used to generate the reference current pattern.

17. The method of claim 16, wherein the difference is at least one amino acid difference in the amino acid sequence of the protein nanopore compared to the amino acid of the protein nanopore in the nanopore system used to generate the reference current pattern.

18. The method of claim 17, wherein the at least one amino acid difference is a substitution, a deletion, or an addition of an amino acid.

19. The method of claim 18, wherein the difference results in a net charge change in the nanopore.

20. The method of claim 1, wherein the molecule/drug is a putative agonist, an antagonist, or a co-factor of enzyme activity.

* * * * *

SEQUENCE LISTING

```
Sequence total quantity: 4
SEQ ID NO: 1           moltype =    length =
SEQUENCE: 1
000

SEQ ID NO: 2           moltype =    length =
SEQUENCE: 2
000

SEQ ID NO: 3           moltype = DNA   length = 13
FEATURE                Location/Qualifiers
source                 1..13
                       mol_type = other DNA
                       organism = synthetic construct
modified_base          5
                       mod_base = OTHER
                       note = abasic residue
SEQUENCE: 3
ttcncccgt acc                                                          13

SEQ ID NO: 4           moltype = DNA   length = 10
FEATURE                Location/Qualifiers
source                 1..10
                       mol_type = other DNA
                       organism = synthetic construct
SEQUENCE: 4
catgattccc                                                             10
```